(12) United States Patent
Lardy et al.

(10) Patent No.: US 8,357,721 B2
(45) Date of Patent: Jan. 22, 2013

(54) SPECIFIC CASPASE-10 INHIBITORS

(75) Inventors: Claude Lardy, Lyons (FR); Marc Lecomte, Lissieu (FR); Thierry Convard, Sathonay-Camp (FR); Catherine Vidal, Lyons (FR)

(73) Assignee: Merck Patent GmbH, Darmstadt (DE)

( * ) Notice: Subject to any disclaimer, the term of this patent is extended or adjusted under 35 U.S.C. 154(b) by 1351 days.

(21) Appl. No.: 11/912,461

(22) PCT Filed: Apr. 6, 2006

(86) PCT No.: PCT/EP2006/003149
§ 371 (c)(1),
(2), (4) Date: Oct. 24, 2007

(87) PCT Pub. No.: WO2006/114190
PCT Pub. Date: Nov. 2, 2006

(65) Prior Publication Data
US 2008/0182906 A1   Jul. 31, 2008

(30) Foreign Application Priority Data

Apr. 25, 2005   (FR) ..................... 05 04134

(51) Int. Cl.
*A01N 41/12*   (2006.01)
*A01N 33/02*   (2006.01)
*A61K 31/16*   (2006.01)
*A61K 31/135*   (2006.01)
(52) U.S. Cl. ........................................ 514/608; 514/646
(58) Field of Classification Search .................. 514/608, 514/646
See application file for complete search history.

(56) References Cited

U.S. PATENT DOCUMENTS

| 5,387,709 | A  | * | 2/1995 | Lardy et al. ............... 558/388 |
| 6,509,499 | B1 |   | 1/2003 | Collonges et al. |
| 7,138,418 | B2 |   | 11/2006 | Flygare et al. |
| 2001/0006965 | A1 |   | 7/2001 | Pamukcu et al. |
| 2003/0216290 | A1 |   | 11/2003 | Lecomte et al. |

FOREIGN PATENT DOCUMENTS

| EP | 0472449 A2 | 2/1992 |
| WO | WO 9828265 A1 | 7/1998 |
| WO | WO 0234201 A2 | 5/2002 |

OTHER PUBLICATIONS

Patani (Chem Reviews, vol. 96, No. 8 (1996) 3147-3176).*

* cited by examiner

*Primary Examiner* — Benjamin Packard
(74) *Attorney, Agent, or Firm* — Millen, White, Zelano & Branigan, P.C.

(57) ABSTRACT

The invention relates to compounds of the general formula (I) wherein R1, R2, R3, R4, R5, R6, i and j have the meanings given in claim 1, and to the use thereof as caspase-10 inhibitors, especially for the treatment of diabetic retinopathy.

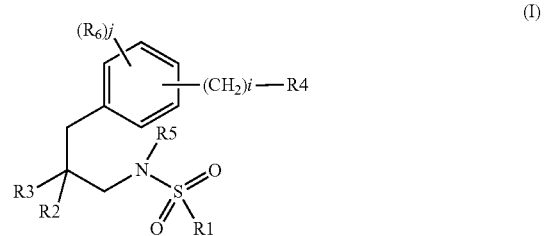

28 Claims, No Drawings

SPECIFIC CASPASE-10 INHIBITORS

Diabetic retinopathy represents one of the most debilitating microvascular complications of diabetes, which can lead in its final stage to blindness (Grange, *La Rétinopathie diabétique* [Diabetic Retinopathy], Masson, Paris, Milan, Barcelona, 1995, p. 632; Frank, Diabetic Retinopathy (Chapter 1), in Progress in Retinal and Eye Research, vol. 14 (No. 2), Elsevier Science Ltd (Great Britain), 1995, pp. 361-3921; Aiello et al., *Diabetes Care,* 21, 1998, 227-293). It is the second cause of acquired blindness in the Western world after age-related macular degeneration (Nathan et al., *Diabetes Care,* 14, 1991, 26-33), and the risk of a diabetic patient becoming blind is estimated at 25 times higher than that of the general population (Kahn et al., *Am. J. Ophthalmol.* 78, 1974, 58-67). At the present time, there is no preventive or curative pharmacological treatment for this complication, the only treatment being retinal photocoagulation by laser or vitreotectomy in the more severe cases (Frank, Diabetic Retinopathy (Chapter 1), in Progress in Retinal and Eye Research, vol. 14 (No. 2), Elsevier Science Ltd (Great Britain), 1995, pp. 361-392; Aiello et al., *Diabetes Care,* 21, 1998, 227-293).

In its early phase, cellular alterations in the retinal capillaries (see FIG. 1) have been demonstrated, especially a selective disappearance of pericytes, altering the numerical ratio of the pericytes relative to the endothelial cells of the retinal capillaries, going from 1 to 1 in the normal situation to 0.3 to 1 in the pathological situation and even 0.1 for the final stages (Cogan et al., *Arch. Ophthalmol.* 60, 1961, 100-112; Kuwabara et al., *Arch. Ophthalmol.* 69, 1963, 492-502). During this phase, death of the pericytes by apoptosis has been detected (Mizutani et al., *J. Clin. Invest.* 97, 1996, 2883-2890; Li et al., *Chin. Med. J.* (Engl.) 110, 1997, 659-663; Podesta et al., *Am. J. Pathol.* 156, 2000, 1025-1032), but the intracellular signalling pathway(s) via which they disappear was (were) not known. The relationship between the reduction in the number of pericytes and the worsening of the clinical signs of retinopathy has recently been documented with the study of a model of mice that are transgenic for the gene for the growth factor PDGF-$\beta$. The mice whose gene is inactivated, PDGF-$\beta$ −/−, have no pericytes and are non-viable; the heterozygous mice in which only one copy has been inactivated, PDGF-$\beta$ +/−, are viable and have 30% fewer pericytes than the wild-type mice, PDGF-$\beta$ +/+. The diabetic heterozygous mice PDGF-$\beta$ +/−, which have fewer pericytes than the diabetic wild-type mice, progress twice as quickly in terms of microvascular impairments quantified by the acellular capillaries, suggesting a direct relationship between the loss of retinal pericytes and the progress of retinopathy (Hammes et al., *Diabetes* 51, 2002, 3107-3112).

Patent application FR 00/13640 (WO 02/34201 A2) describes the clarification of this chain of events leading to apoptosis of the pericytes induced by AGEs (Advanced Glycation End products). One series of targets—among which is caspase-10—have been identified, which allow a pharmacological intervention in order to prevent their disappearance, and the invention relates to the use of inhibitors of these targets, used alone or in combination, to eradicate the process of loss of the pericytes by apoptosis observed in the early phase of diabetic retinopathy. The use of such pharmacological inhibitors, such as those of caspase-10, should be beneficial for the treatment or prevention of diabetic retinopathy, by protecting the pericytes against apoptosis and thus slowing down its progress towards the final stages of this complication, which are the most serious.

The present invention relates to novel selective caspase-10 inhibitors of the formula (I), which are active at 5-25 µM, non-cytotoxic, and which inhibit the AGE-induced apoptosis of pericytes, for the treatment of or preventing diabetic retinopathy in its early stage.

Diabetic retinopathy is an evolutive diabetic complication, passing from a "basal" stage (background retinopathy) to a final phase known as "proliferative retinopathy", in which there is formation of new fragile retinal vessels, leading to severe haemorrhaging, occasionally with detachment of the retina, and to loss of vision (Grange, *La Rétinopathie diabétique* [Diabetic Retinopathy], Masson, Paris, Milan, Barcelona, 1995, p. 632; Frank, *Diabetic Retinopathy* (Chapter 1), in Progress in Retinal and Eye Research, vol. 14 (No. 2), Elsevier Science Ltd (Great Britain), 1995, pp. 361-392). In background retinopathy, the microvascular lesions are characterised by microaneurisms, small point haemorrhages, exudates and venous dilations (Palmberg, Diabetic Retinopathy, Diabetes 26, 1977, 703-709; ETDRS, *Early Treatment Diabetic Retinopathy Study Research Group,* Report No. 10, *Ophthalmology* 98, 1991, 786-791). This background retinopathy may remain clinically silent for a long time. At this "background" stage, cellular and structural alterations of the retinal capillaries have been noted, from examination of the retinas of diabetic patients collected post-mortem and compared with retinas of normal individuals of comparable ages.

The retinal capillaries are lined with endothelial cells, on the luminal side of the vessel, and with pericytes (or wall cells) located on the exterior and buried in the basal membrane of the vessel. FIG. 1 illustrates a retinal capillary.

In the human retina or the rat retina, the numerical ratio of the pericytes to the endothelial cells is 1 to 1 (Kuwabara et al., *Arch. Ophthalmol.* 69, 1963, 492-502). The impairments observed at this early stage consist of thickening of the basal membrane of the capillaries (Friedenwald, *Diabetic Retinopathy, Am. J. Ophthalmol.* 33, 1950, 1187-1199) and selective disappearance of the pericytes (Cogan et al., *Arch. Ophthalmol.* 60, 1961, 100-112; Kuwabara et al., *Arch. Ophthalmol.* 69, 1963, 492-502), leading to a ratio of the number of pericytes to endothelial cells of less than 1 to 1 (Kuwabara et al., *Arch. Ophthalmol.* 69, 1963, 492-502). Recent studies performed using human retinas removed post-mortem from long-term diabetic patients have made it possible to show that the pericytes died by apoptosis, programmed cell death, rather than by necrosis, sudden death observed following a toxic attack (Mizutani et al., *J. Clin. Invest.* 97, 1996, 2883-2890; Li et al., *Chin. Med. J.* (Engl.) 110, 1997, 659-663; Podesta et al., *Am. J. Pathol.* 156, 2000, 1025-1032). Detection of the apoptotic pericytes was performed in situ, on the whole retinas by a technique of staining of the nuclei of the cells entering into apoptosis, the TUNEL method (Terminal Deoxynucleotidyl Transferase Mediated dUDP Nick-end Labeling) (Mizutani et al., *J. Clin. Invest.* 97, 1996, 2883-2890). Another recent study has also shown that anti-pericyte auto-antibodies were detectable in type 2 diabetic patients and that they were associated with the early stages of diabetic retinopathy, suggesting an expression of novel antigens by the "active" pericytes during diabetes (Nayak et al., *Diabetologia* 46, 2003, 511-513).

The underlying cell mechanisms via which the pericytes die by apoptosis are still largely unknown. The studies undertaken in the past by The Diabetes Control Complications Trial Research Group (DCCT), *N. Engl. J. Med.* 239, 1993, 977-986) or the UK Prospective Diabetes Study Group (UKPDS), *Lancet* 352 (33, 1998a, 837-853 and 34, 1998b, 854-865) have shown the key role of the control of hyperglycaemia in the development of diabetic retinopathy. A possible mechanism via which glucose can lead to the death of the pericytes is the increased production and accumulation of advanced glycation end products or AGEs formed by non-enzymatic glycosylation—or glycation—of proteins, DNA or lipids (Maillard reaction) which have been demonstrated in many studies during diabetes (Thornalley, *Clin. Lab.* 45, 1999, 261-273). The amount of AGEs measured in the skin of diabetic patients is moreover strongly correlated with the severity of the vascular complications (Beisswenger et al., *Diabetes* 44, 1995, 824-829).

AGEs are formed after a complex cascade of reactions that begins with the binding of reducing sugars to proteins: a sugar, in open form, reacts first with the free amine group of basic amino acids contained in the proteins (lysine, arginine), leading to the formation of a Schiff's base, which is subsequently stabilised as an Amadori product. FIG. 2 illustrates the Maillard route.

These steps are reversible and dependent on the concentration of the substrates (proteins and sugars). Once formed, the Amadori product undergoes a series of changes that leads either to oxidative fragmentation and to the formation of "glycoxidation" products, such as carboxymethyllysine (CML), or to the formation of dicarbonyls, such as 3-deoxyglucosone, which may in turn react with the free amines of proteins and thus propagate the Maillard reaction (Thornalley, *Clin. Lab.* 45, 1999, 261-273). The AGEs formed during the development of diabetes, and which accumulate in the proteins with a long service life, originate from the reaction with glucose, but also from other reactive dicarbonyls derived from glucose, for instance methylglyoxal. Methylglyoxal, formed by the fragmentation of triose phosphates and the oxidation of acetone in the liver (by means of monooxygenases) is increased in the plasma of diabetics (McLellan et al., *Clin. Sci.* 7, 1994, 21-29). Furthermore, the AGEs of proteins formed after reaction with methylglyoxal are described as major products observed during diabetes (Degenhardt et al, *Cell. Mol. Biol.* 44, 1998, 1139-1145) and the formation of AGEs on the intracellular proteins with methylglyoxal appears to be a major route of formation in the cells (Nishikawa et al., *Nature* 404, 2000, 787-790); Shinohara et al., *J. Clin. Invest.* 101, 1998, 1142-1147). The present inventors have described AGEs formed from methylglyoxal in FR 00/13640 (WO 02/34201 A2) and shown that they induce apoptosis of the pericytes and that caspase-10 is involved at an early stage in the biochemical cascade leading to the death of the pericytes.

The retinal pericytes are buried in the basal membrane of the capillaries and in contact with the proteins with a long service life that constitute it and which, in diabetic patients, accumulate Amadori products (Schalkwijk et al., *Diabetes* 48, 1999, 2446-2453) and AGEs (Endo et al., Horm. Metab. Res. 33, 2001, 317-322) detectable in the capillaries. The AGE receptors, for instance RAGE (Receptor for Advanced Glycation End-Products) (Brett et al., *Am. J. Pathol.* 143, 1993, 1699-1712; Yonekura et al., *Biochem. J.* 370, 2003, 1097-1109), p. 60 p. 90 (Stitt et al., Am. J. Pathol. 150, 1997, 523-531; Chibber et al., *Diabetologia* 40, 1997, 156-164) have been described as being present on the plasma membrane of pericytes. The co-localisation of AGEs and of the AGE receptors present on the retinal pericytes indicates that the AGEs might participate in the death of the pericytes observed in the early stages of retinopathy. The possibility of a direct toxic effect of the AGEs on pericytes arises from experiments performed on animals, in which the intravenous infusion of preformed AGEs in non-diabetic rats causes a 25% reduction in the number of pericytes present in the retinal capillaries after two weeks of treatment (Xu et al., *Graefe's Arch. Clin. Exp. Ophthalmol.* 241, 2003, 56-62) with accumulation of the AGEs inside and around the retinal pericytes (Stitt et al., *Am. J. Pathol.* 150, 1997, 523-531). An indirect argument for the effect of AGEs on the death of the retinal pericytes arises from pharmacological studies on animals to test the effect of glycation inhibitors, such as aminoguanidine or pyridoxamine on the progress of retinopathy. The treatment of diabetic rats for 29 weeks with pyridoxamine prevents the death of the pericytes observed in the untreated rats and also the formation of AGEs (N-($\epsilon$)-(carboxymethyl)lysine) in the retinal capillaries (Stitt et al., *Diabetes* 51, 2002, 2826-2832). Similarly, diabetic rats treated for 26 weeks with aminoguanidine show a reduced accumulation of AGEs in the retinal capillaries and also a slowed progress of retinopathy measured by various markers, such as the loss of the pericytes, microaneurisms and the 80% reduced formation of acellular capillaries (Hammes et al., *Proc. Natl Acad. Sci. USA* 88, 1991, 11555-11558).

The identification of caspase-10 in the biochemical cascade leading to the AGE-induced apoptosis of pericytes and the use of specific inhibitors forming the subject of the present invention would make it possible to treat or prevent diabetic retinopathy at an early stage by slowing down the loss of pericytes by apoptosis and also the progress of retinopathy towards the clinical stages of "proliferative retinopathy". It should be pointed out, however, that (a) the caspase-10 inhibitors that are the subject of the invention offer a means of treatment or prevention both of basal retinopathy (less than two microaneurisms per ocular fundus, and of clinically established retinopathy, and that (b) the term "diabetic retinopathy" used in the invention denotes both basal retinopathy and clinically established retinopathy.

Compounds similar to the compounds of the invention have been described in EP 0 472 449; these compounds form the subject of a disclaimer. However, this document does not in any way describe the use for the treatment of retinopathy.

According to a first subject, the present invention thus relates to the use of a compound of the formula (I):

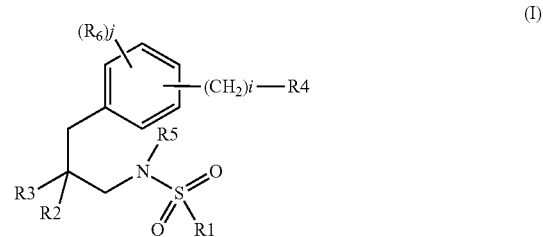

for the preparation of a medicament for the prevention of or treating retinopathy, in which formula (I):

R1 represents a group of the formula: —X—(Y)$_m$, in which:

—X— represents an aryl, cycloalkyl, heteroaryl, alkyl or heterocyclyl group;

Each of the groups Y, which may be identical or different, independently represents a halogen atom or an -alkyl, —O-alkyl, —CO-alkyl, —NO$_2$, —O-perhaloalkyl, —S(O)$_q$-alkyl or -perhaloalkyl group, or two groups Y together form an aryl or heteroaryl group fused to the phenyl nucleus to which they are attached;

m represents an integer chosen from 0, 1, 2, 3, 4 and 5;

R2 and R3 together form a cycloalkyl or heterocyclyl group optionally substituted by one or more alkyl groups;

R4 represents a group of the formula -Z-(alkyl)$_n$-T$_p$ in which

-Z- represents —O— or a group —S(O)$_q$— or, if n=p=0, a halogen atom or an —OH group;

T represents a cycloalkyl, heterocyclyl or heteroaryl group;

n represents an integer chosen from 0 and 1;

p represents an integer chosen from 0 and 1;

i represents an integer greater than or equal to 2;

R5 represents a hydrogen atom or an alkyl group, optionally substituted by one or more cycloalkyl groups;

Each of the groups R6, which may be identical or different, independently represents a group chosen from alkyl, O-alkyl, a halogen atom and a —CN, —NO$_2$, —CO-alkyl, —CO$_2$R, —NRR', —O-perhaloalkyl or -perhaloalkyl group;

j represents an integer chosen between 0, 1, 2, 3 and 4;

R and R', which may be identical or different, independently represent a hydrogen atom or an alkyl group;

q represents an integer chosen from 0, 1 and 2;

and also the tautomeric, enantiomeric, diastereoisomeric and epimeric forms, the esters and the pharmaceutically acceptable salts.

It is especially preferred to use compounds of the formula (I) for which:

R1 represents a phenyl group optionally substituted by one or more groups, which may be identical or different, chosen from a halogen atom and an -alkyl, —O-alkyl, —CO-alkyl, —NO$_2$, —O-perhaloalkyl, —S(O)$_q$-alkyl or -perhaloalkyl group, or two substituents together form a phenyl or pyridyl group fused to the phenyl nucleus to which they are attached; or R1 represents a cycloalkyl, heteroaryl or alkyl group; and/or R2 and R3 together form a cycloalkyl group, optionally substituted by one or more alkyl groups; or R2 and R3 together form a heterocyclyl group; and/or R4 represents a group of the formula -Z-(alkyl)$_n$-T$_p$ in which Z represents —O— or a group —S(O)$_q$— or, if n=p=0, a halogen atom or an —OH group;

i represents 2;

n represents an integer chosen from 0 and 1;

p represents an integer chosen from 0 and 1;

T represents a cycloalkyl, heterocyclyl or heteroaryl group; and/or

R5 represents a hydrogen atom or an alkyl group, optionally substituted by one or more cycloalkyl groups; and/or R and R', which may be identical or different, independently represent a hydrogen atom or an alkyl group; and/or q represents an integer chosen from 0, 1 and 2;

and also the tautomeric, enantiomeric, diastereoisomeric and epimeric forms, the esters and the pharmaceutically acceptable salts.

More preferentially, it is preferred to use a compound of the formula (I) for which:

R1 represents a phenyl group optionally substituted by one or more groups, which may be identical or different, chosen from a halogen atom and an -alkyl, —O-alkyl, —CO-alkyl, —S(O)$_q$-alkyl, —NO$_2$ or -perhaloalkyl group, or two substituents together form a phenyl group fused to the phenyl nucleus to which they are attached; and/or R2 and R3 together form a cycloalkyl group; and/or R4 represents a group of the formula -Z-(alkyl)$_n$-T$_p$ in which Z represents —O— or a group —S(O)$_q$— or, if n=p=0, a halogen atom;

n represents an integer chosen from 0 and 1;

p represents an integer chosen from 0 and 1;

q represents 0 or 2;

T represents a cycloalkyl or heterocyclyl group; and/or i=2;

R5 represents a hydrogen atom; and/or j=0;

and also the tautomeric, enantiomeric, diastereoisomeric and epimeric forms, the esters and the pharmaceutically acceptable salts.

Preferably, the group —(CH$_2$)$_i$R4 is in the para position.

Preferably, R2 and R3 form a cyclopentyl or cyclobutyl group, more preferentially cyclobutyl.

Preferably, R1 represents a phenyl group substituted by at least one halogen atom.

Preferably, Z represents a group —S(O)$_q$— in which q=0 or 2.

As compounds of the formula (I) that are useful according to the invention, mention may be made of the compounds chosen from:

2,4-dichloro-N-[(1-{4-[2-(cyclopropylmethoxy)ethyl]benzyl}cyclobutyl)-methyl]benzenesulfonamide;

4-chloro-N-[(1-{4-[2-(cyclopropylmethoxy)ethyl]benzyl}cyclobutyl)methyl]-benzenesulfonamide;

N-[(1-{4-[2-(cyclopropylmethoxy)ethyl]benzyl}cyclobutyl)methyl]-4-methyl-benzenesulfonamide;

N-[(1-{4-[2-(cyclopropylmethoxy)ethyl]benzyl}cyclobutyl)methyl]naphthalene-1-sulfonamide;

N-[(1-{4-[2-(cyclopropylmethoxy)ethyl]benzyl}cyclobutyl)methyl]-4-methoxy-benzenesulfonamide;

4-chloro-N-[(1-{4-[2-(cyclopentyloxy)ethyl]benzyl}cyclobutyl)methyl]benzenesulfonamide;

2,4-dichloro-N-[(1-{4-[2-(cyclopentyloxy)ethyl]benzyl}cyclobutyl)methyl]benzenesulfonamide;

N-[(1-{4-[2-(cyclopentyloxy)ethyl]benzyl}cyclobutyl)methyl]-4-methylbenzenesulfonamide;

N-[(1-{4-[2-(cyclopentyloxy)ethyl]benzyl}cyclobutyl)methyl]-4-methoxybenzenesulfonamide;

N-[(1-{4-[2-(cyclopentyloxy)ethyl]benzyl}cyclobutyl)methyl]naphthalene-1-sulfonamide;

4-chloro-N-[(1-{4-[2-(cyclopentylthio)ethyl]benzyl}cyclobutyl)methyl]benzenesulfonamide;

2,4-dichloro-N-[(1-{4-[2-(cyclopentylthio)ethyl]benzyl}cyclobutyl)methyl]benzenesulfonamide;

N-[(1-{4-[2-(cyclopentylthio)ethyl]benzyl}cyclobutyl)methyl]-4-methylbenzenesulfonamide;

N-[(1-{4-[2-(cyclopentylthio)ethyl]benzyl}cyclobutyl)methyl]-4-methoxybenzenesulfonamide;

N-[(1-{4-[2-(cyclopentylthio)ethyl]benzyl}cyclobutyl)methyl]naphthalene-1-sulfonamide;

4-chloro-N-[(1-{4-[2-(methylthio)ethyl]benzyl}cyclobutyl)methyl]benzenesulfonamide;

2,4-dichloro-N-[(1-{4-[2-(methylthio)ethyl]benzyl}cyclobutyl)methyl]benzenesulfonamide;

4-methyl-N-[(1-{4-[2-(methylthio)ethyl]benzyl}cyclobutyl)methyl]benzenesulfonamide;

4-methoxy-N-[(1-{4-[2-(methylthio)ethyl]benzyl}cyclobutyl)methyl]benzenesulfonamide;

N-[(1-{4-[2-(methylthio)ethyl]benzyl}cyclobutyl)methyl]naphthalene-1-sulfonamide;

4-chloro-N-[(1-{4-[2-(cyclopentylsulfonyl)ethyl]benzyl}cyclobutyl)methyl]benzenesulfonamide;

2,4-dichloro-N-[(1-{4-[2-(cyclopentylsulfonyl)ethyl]benzyl}cyclobutyl)methyl]-benzenesulfonamide;

N-[(1-{4-[2-(cyclopentylsulfonyl)ethyl]benzyl}cyclobutyl)methyl]-4-methyl-benzenesulfonamide;

N-[(1-{4-[2-(cyclopentylsulfonyl)ethyl]benzyl}cyclobutyl)methyl]-4-methoxy-benzenesulfonamide;

N-[(1-{4-[2-(cyclopentylsulfonyl)ethyl]benzyl}cyclobutyl)methyl]naphthalene-1-sulfonamide;

4-chloro-N-[(1-{4-[2-(methylsulfonyl)ethyl]benzyl}cyclobutyl)methyl]benzene-sulfonamide;

2,4-dichloro-N-[(1-{4-[2-(methylsulfonyl)ethyl]benzyl}cyclobutyl)methyl]benzenesulfonamide;

4-methyl-N-[(1-{4-[2-(methylsulfonyl)ethyl]benzyl}cyclobutyl)methyl]benzenesulfonamide;

4-methoxy-N-[(1-{4-[2-(methylsulfonyl)ethyl]benzyl}cyclobutyl)methyl]benzenesulfonamide;

N-[(1-{4-[2-(methylsulfonyl)ethyl]benzyl}cyclobutyl)methyl]naphthalene-1-sulfonamide;

N-({1-[4-(2-tert-butoxyethyl)benzyl]cyclopentyl}methyl)-4-methylbenzenesulfonamide;
4-chloro-N-[(1-{4-[2-(pyrid-2-yloxy)ethyl]benzyl}cyclopentyl)methyl]benzenesulfonamide;
4-chloro-N-({1-[4-(2-hydroxyethyl)benzyl]cyclopentyl}methyl)benzenesulfonamide;
3-chloro-N-({1-[4-(2-hydroxyethyl)benzyl]cyclopentyl}methyl)benzenesulfonamide;
4-acetyl-N-({1-[4-(2-hydroxyethyl)benzyl]cyclopentyl}methyl)benzenesulfonamide;
N-({1-[4-(2-hydroxyethyl)benzyl]cyclopentyl}methyl)-4-(methylsulfonyl)benzenesulfonamide;
N-({1-[4-(2-hydroxyethyl)benzyl]cyclopentyl}methyl)-4-(trifluoromethoxy)-benzenesulfonamide;
4-chloro-N-({1-[4-(2-hydroxyethyl)benzyl]-3,3-dimethylcyclobutyl}methyl)-benzenesulfonamide;
N-({1-[4-(2-hydroxyethyl)benzyl]cyclopentyl}methyl)-1H-imidazole-5-sulfonamide;
4-chloro-N-({1-[4-(2-hydroxyethyl)benzyl]cyclohexyl}methyl)benzenesulfonamide;
N-({1-[4-(2-hydroxyethyl)benzyl]cyclopentyl}methyl)-3-methylquinoline-8-sulfonamide;
4-chloro-N-({1-[4-(2-hydroxyethyl)benzyl]-2,2,3,3-tetramethylcyclopropyl}-methyl)benzenesulfonamide;
N-({1-[4-(2-hydroxyethyl)benzyl]cyclopentyl}methyl)-4-(methylthio)benzenesulfonamide;
4-chloro-N-({1-[3-(2-hydroxyethyl)benzyl]cyclopentyl}methyl)benzenesulfonamide;
3,4-dichloro-N-({1-[4-(2-hydroxyethyl)benzyl]cyclopentyl}methyl)benzenesulfonamide;
2,4-dichloro-N-({1-[4-(2-hydroxyethyl)benzyl]cyclopentyl}methyl)benzenesulfonamide;
N-({1-[4-(2-hydroxyethyl)benzyl]cyclopentyl}methyl)-4-methoxybenzenesulfonamide;
4-chloro-N-({4-[4-(2-hydroxyethyl)benzyl]tetrahydro-2H-pyran-4-yl}methyl)-benzenesulfonamide;
N-({1-[4-(2-hydroxyethyl)benzyl]cyclopentyl}methyl)-4-(trifluoromethyl)benzenesulfonamide;
N-({1-[4-(2-hydroxyethyl)benzyl]cyclopentyl}methyl)-3-(trifluoromethyl)benzenesulfonamide;
N-({1-[4-(2-hydroxyethyl)benzyl]cyclopentyl}methyl)naphthalene-2-sulfonamide;
N-({1-[4-(2-hydroxyethyl)benzyl]cyclopentyl}methyl)-4-nitrobenzenesulfonamide;
4-cyclohexyl-N-({1-[4-(2-hydroxyethyl)benzyl]cyclopentyl}methyl)benzenesulfonamide;
N-({1-[4-(2-hydroxyethyl)benzyl]cyclopentyl}methyl)pyridine-3-sulfonamide;
4-chloro-N-({1-[4-(2-hydroxyethyl)benzyl]cyclopropyl}methyl)benzenesulfonamide;
4-chloro-N-({1-[4-(2-hydroxyethyl)benzyl]cyclobutyl}methyl)benzenesulfonamide;
N-({1-[4-(2-hydroxyethyl)benzyl]cyclobutyl}methyl)-4-methylbenzenesulfonamide;
2,3,4,5,6-pentafluoro-N-({1-[4-(2-hydroxyethyl)benzyl]cyclopentyl}methyl)-benzenesulfonamide;
N-({1-[4-(2-hydroxyethyl)benzyl]cyclopentyl}methyl)-4-methylbenzenesulfonamide;
N-({1-[4-(2-hydroxyethyl)benzyl]cyclopentyl}methyl)-4-methylbenzenesulfonamide;
3,4,5-trifluoro-N-({1-[4-(2-hydroxyethyl)benzyl]cyclopentyl}methyl)benzenesulfonamide;
3,5-dichloro-N-({1-[4-(2-hydroxyethyl)benzyl]cyclopentyl}methyl)benzenesulfonamide;
N-({1-[4-(2-hydroxyethyl)benzyl]cyclopentyl}methyl)-3-methylbenzenesulfonamide;
4-fluoro-N-({1-[4-(2-hydroxyethyl)benzyl]cyclopentyl}methyl)benzenesulfonamide;
4-chloro-N-({1-[4-(2-hydroxyethyl)benzyl]cyclopentyl}methyl)-3-(trifluoromethyl)benzenesulfonamide;
N-({1-[4-(2-chloroethyl)benzyl]cyclobutyl}methyl)-2,3,4,5,6-pentafluorobenzenesulfonamide;
N-({1-[4-(2-hydroxyethyl)benzyl]cyclopentyl}methyl)-4-nitro-3-(trifluoromethyl)benzenesulfonamide;
N-(cyclopropylmethyl)-N-({1-[4-(2-hydroxyethyl)benzyl]cyclobutyl}methyl)-4-methylbenzenesulfonamide;
4-chloro-N-(cyclopropylmethyl)-N-({1-[4-(2-hydroxyethyl)benzyl]cyclobutyl}-methyl)benzenesulfonamide.

As compounds of the formula (I) that are useful according to the invention, the preferred compounds are those chosen from:

2,4-dichloro-N-[(1-{4-[2-(cyclopropylmethoxy)ethyl]benzyl}cyclobutyl)methyl]benzenesulfonamide
N-[(1-{4-[2-(cyclopropylmethoxy)ethyl]benzyl}cyclobutyl)methyl]-4-methoxybenzenesulfonamide
2,4-dichloro-N-[(1-{4-[2-(cyclopentylthio)ethyl]benzyl}cyclobutyl)methyl]benzenesulfonamide
2,4-dichloro-N-[(1-{4-[2-(methylthio)ethyl]benzyl}cyclobutyl)methyl]benzenesulfonamide
2,4-dichloro-N-[(1-{4-[2-(cyclopentylsulfonyl)ethyl]benzyl}cyclobutyl)methyl]benzenesulfonamide
2,4-dichloro-N-[(1-{4-[2-(methylsulfonyl)ethyl]benzyl}cyclobutyl)methyl]benzenesulfonamide
N-[(1-{4-[2-(methylsulfonyl)ethyl]benzyl}cyclobutyl)methyl]naphthalene-1-sulfonamide
4-chloro-N-({1-[4-(2-hydroxyethyl)benzyl]cyclopentyl}methyl)benzenesulfonamide
3-chloro-N-({1-[4-(2-hydroxyethyl)benzyl]cyclopentyl}methyl)benzenesulfonamide
4-acetyl-N-({1-[4-(2-hydroxyethyl)benzyl]cyclopentyl}methyl)benzenesulfonamide
N-({1-[4-(2-hydroxyethyl)benzyl]cyclopentyl}methyl)-4-(methylsulfonyl)benzenesulfonamide
N-({1-[4-(2-hydroxyethyl)benzyl]cyclopentyl}methyl)-4-(methylthio)benzenesulfonamide
3,4-dichloro-N-({1-[4-(2-hydroxyethyl)benzyl]cyclopentyl}methyl)benzenesulfonamide
2,4-dichloro-N-({1-[4-(2-hydroxyethyl)benzyl]cyclopentyl}methyl)benzenesulfonamide
N-({1-[4-(2-hydroxyethyl)benzyl]cyclopentyl}methyl)-4-methoxybenzenesulfonamide
N-({1-[4-(2-hydroxyethyl)benzyl]cyclopentyl}methyl)-4-(trifluoromethyl)benzenesulfonamide
N-({1-[4-(2-hydroxyethyl)benzyl]cyclopentyl}methyl)-3-(trifluoromethyl)benzenesulfonamide
N-({1-[4-(2-hydroxyethyl)benzyl]cyclopentyl}methyl)naphthalene-2-sulfonamide
N-({1-[4-(2-hydroxyethyl)benzyl]cyclopentyl}methyl)-4-nitrobenzenesulfonamide
4-chloro-N-({1-[4-(2-hydroxyethyl)benzyl]cyclobutyl}methyl)benzenesulfonamide
N-({1-[4-(2-hydroxyethyl)benzyl]cyclobutyl}methyl)-4-methylbenzenesulfonamide
2,3,4,5,6-pentafluoro-N-({1-[4-(2-hydroxyethyl)benzyl]cyclopentyl}methyl)benzenesulfonamide
N-({1-[4-(2-hydroxyethyl)benzyl]cyclopentyl}methyl)-4-methylbenzenesulfonamide
3,4,5-trifluoro-N-({1-[4-(2-hydroxyethyl)benzyl]cyclopentyl}methyl)benzenesulfonamide
3,5-dichloro-N-({1-[4-(2-hydroxyethyl)benzyl]cyclopentyl}methyl)benzenesulfonamide N-({1-[4-(2-hydroxyethyl)benzyl]cyclopentyl}methyl)-3-methylbenzenesulfonamide 4-chloro-N-({1-[4-(2-hydroxyethyl)benzyl]cyclopentyl}methyl)-3-(trifluoromethyl)-benzenesulfonamide N-({1-[4-(2-chloroethyl)benzyl]cyclobutyl}methyl)-2,3,4,5,6-pentafluorobenzenesulfonamide, and also the tautomeric, enantiomeric, diastereoisomeric and epimeric forms, the esters and the pharmaceutically acceptable salts.

According to another subject, the present invention also relates to the compounds of the formula (I):

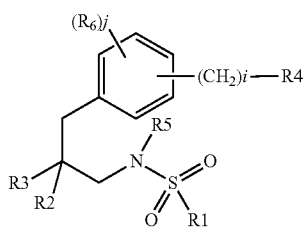

(I)

in which:

R1 represents a group of the formula: —X—(Y)$_m$, in which:

X represents an aryl, cycloalkyl, heteroaryl, alkyl or heterocyclyl group; each of the groups Y, which may be identical or different, independently represents a halogen atom or an -alkyl, —O-alkyl, —CO-alkyl, —NO$_2$, —S(O)$_q$-alkyl, —O-per-haloalkyl or -perhaloalkyl group, or two groups Y together form an aryl or heteroaryl group fused to the phenyl nucleus to which they are attached;

m represents an integer chosen from 0, 1, 2, 3, 4 and 5;

R2 and R3 together form a cycloalkyl or heterocyclyl group optionally substituted by one or more alkyl groups;

R4 represents a group of the formula -Z-(alkyl)$_n$-T$_p$ in which

Z represents —O— or a group —S(O)$_q$— or, if n=p=0, a halogen atom;

n represents an integer chosen from 0 and 1;

p represents an integer chosen from 0 and 1;

T represents a cycloalkyl, heterocyclyl or heteroaryl group;

i represents an integer greater than or equal to 2;

R5 represents a hydrogen atom or an alkyl group, optionally substituted by one or more cycloalkyl groups;

Each of the groups R6, which may be identical or different, independently represents a group chosen from alkyl, O-alkyl and a halogen atom, or a —CN, —NO$_2$, —CO-alkyl, —CO$_2$R, —NRR', —O-perhaloalkyl or -perhaloalkyl group;

j represents an integer chosen between 0, 1, 2, 3 and 4;

R and R', which may be identical or different, independently represent a hydrogen atom or an alkyl group;

q represents an integer chosen from 0, 1 and 2;

and also the tautomeric, enantiomeric, diastereoisomeric and epimeric forms, the esters and the pharmaceutically acceptable salts, with the exception of the compounds for which R4 represents an —OH group or an —O-tetrahydropyran group.

The compounds of the formula (I) that are especially preferred are those for which:

R1 represents a phenyl group optionally substituted by one or more groups, which may be identical or different, chosen from a halogen atom and an -alkyl, —O-alkyl, —CO-alkyl, —NO$_2$, —S(O)$_q$-alkyl, —O-perhaloalkyl or -perhaloalkyl group, or two substituents together form a phenyl or pyridyl group fused to the phenyl nucleus to which they are attached; or R1 represents a cycloalkyl, heteroaryl or alkyl group; and/or R2 and R3 together form a cycloalkyl group, optionally substituted by one or more alkyl groups; or R2 and R3 together form a heterocyclyl group; and/or R4 represents a group of the formula -Z-(alkyl)$_n$-T$_p$ in which Z represents —O— or a group —S(O)$_q$— or, if n=p=0, a halogen atom;

n represents an integer chosen from 0 and 1;

p represents an integer chosen from 0 and 1;

T represents a cycloalkyl, heterocyclyl or heteroaryl group; and/or i=2;

R5 represents a hydrogen atom or an alkyl group, optionally substituted by one or more cycloalkyl groups; and/or j=0;

R and R', which may be identical or different, independently represent a hydrogen atom or an alkyl group; and/or q represents an integer chosen from 0, 1 and 2;

and also the tautomeric, enantiomeric, diastereoisomeric and epimeric forms, the esters and the pharmaceutically acceptable salts, with the exception of the compounds for which R4 represents an —OH group or an —O-tetrahydropyran group.

More preferentially, a compound of the formula (I) that is preferred is one for which:

R1 represents a phenyl group optionally substituted by one or more groups, which may be identical or different, chosen from a halogen atom and an -alkyl, —O-alkyl, —S(O)$_2$-alkyl or -perhaloalkyl group, or two substituents together form a phenyl group fused to the phenyl nucleus to which they are attached; and/or R2 and R3 together form a cycloalkyl group; and/or R4 represents a group of the formula -Z-(alkyl)$_n$-T$_p$ in which Z represents —O— or a group —S(O)$_q$— or, if n=p=0, a halogen atom;

n represents an integer chosen from 0 and 1;

p represents an integer chosen from 0 and 1;

q represents 0 or 2;

T represents a cycloalkyl or heterocyclyl group; and/or

R5 represents a hydrogen atom; and/or i=2; and/or j=0; and/or and also the tautomeric, enantiomeric, diastereoisomeric and epimeric forms, the esters and the pharmaceutically acceptable salts, with the exception of the compounds for which R4 represents an —OH or —O-tetrahydropyran group.

Preferably, the group —(CH$_2$)$_i$R4 is in the para position relative to the group

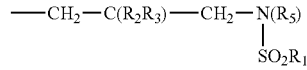

3 form a cyclopentyl or cyclobutyl group, more preferentially a cyclobutyl.

Preferably, R1 represents a phenyl group substituted by at least one halogen atom.

Preferably, Z represents a group —S(O)$_q$ in which q=0 or 2.

As compounds of the formula (I) according to the invention, mention may be made of any compound chosen from:

2,4-dichloro-N-[(1-{4-[2-(cyclopropylmethoxy)ethyl]
benzyl}cyclobutyl)-methyl]benzenesulfonamide;
4-chloro-N-[(1-{4-[2-cyclopropylmethoxy)ethyl]
benzyl}cyclobutyl)methyl]benzenesulfonamide;
N-[(1-{4-[2-(cyclopropylmethoxy)ethyl]benzyl}cyclobutyl)
methyl]-4-methyl-benzenesulfonamide;
N-[(1-{4-[2-(cyclopropylmethoxy)ethyl]benzyl}cyclobutyl)
methyl]naphthalene-1-sulfonamide;
N-[(1-{4-[2-(cyclopropylmethoxy)ethyl]benzyl}cyclobutyl)
methyl]-4-methoxy-benzenesulfonamide;
4-chloro-N-[(1-{4-[2-(cyclopentyloxy)ethyl]
benzyl}cyclobutyl)methyl]benzenesulfonamide;
2,4-dichloro-N-[(1-{4-[2-(cyclopentyloxy)ethyl]
benzyl}cyclobutyl)methyl]benzenesulfonamide;
N-[(1-{4-[2-(cyclopentyloxy)ethyl]benzyl}cyclobutyl)methyl]-4-methylbenzenesulfonamide;
N-[(1-{4-[2-(cyclopentyloxy)ethyl]benzyl}cyclobutyl)methyl]-4-methoxybenzenesulfonamide;
N-[(1-{4-[2-(cyclopentyloxy)ethyl]benzyl}cyclobutyl)methyl]naphthalene-1-sulfonamide;
4-chloro-N-[(1-{4-[2-(cyclopentylthio)ethyl]
benzyl}cyclobutyl)methyl]benzenesulfonamide;
2,4-dichloro-N-[(1-{4-[2-(cyclopentylthio)ethyl]
benzyl}cyclobutyl)methyl]benzenesulfonamide;
N-[(1-{4-[2-(cyclopentylthio)ethyl]benzyl}cyclobutyl)methyl]-4-methylbenzenesulfonamide;
N-[(1-{4-[2-(cyclopentylthio)ethyl]benzyl}cyclobutyl)methyl]-4-methoxybenzenesulfonamide;
N-[(1-{4-[2-(cyclopentylthio)ethyl]benzyl}cyclobutyl)methyl]naphthalene-1-sulfonamide;
4-chloro-N-[(1-{4-[2-(methylthio)ethyl]benzyl}cyclobutyl)
methyl]benzenesulfonamide;
2,4-dichloro-N-[(1-{4-[2-(methylthio)ethyl]
benzyl}cyclobutyl)methyl]benzenesulfonamide;
4-methyl-N-[(1-{4-[2-(methylthio)ethyl]benzyl}cyclobutyl)
methyl]benzenesulfonamide;
4-methoxy-N-[(1-{4-[2-(methylthio)ethyl]
benzyl}cyclobutyl)methyl]benzenesulfonamide;
N-[(1-{4-[2-(methylthio)ethyl]benzyl}cyclobutyl)methyl]
naphthalene-1-sulfonamide;
4-chloro-N-[(1-{4-[2-(cyclopentylsulfonyl)ethyl]
benzyl}cyclobutyl)methyl]benzenesulfonamide;
2,4-dichloro-N-[(1-{4-[2-(cyclopentylsulfonyl)ethyl]
benzyl}cyclobutyl)methyl]-benzenesulfonamide;
N-[(1-{4-[2-(cyclopentylsulfonyl)ethyl]benzyl}cyclobutyl)
methyl]-4-methylbenzenesulfonamide;
N-[(1-{4-[2-(cyclopentylsulfonyl)ethyl]benzyl}cyclobutyl)
methyl]-4-methoxy-benzenesulfonamide;
N-[(1-{4-[2-(cyclopentylsulfonyl)ethyl]benzyl}cyclobutyl)
methyl]naphthalene-1-sulfonamide;
4-chloro-N-[(1-{4-[2-(methylsulfonyl)ethyl]
benzyl}cyclobutyl)methyl]benzene-sulfonamide;
2,4-dichloro-N-[(1-{4-[2-(methylsulfonyl)ethyl]
benzyl}cyclobutyl)methyl]benzenesulfonamide;
4-methyl-N-[(1-{4-[2-(methylsulfonyl)ethyl]
benzyl}cyclobutyl)methyl]benzenesulfonamide;
4-methoxy-N-[(1-{4-[2-(methylsulfonyl)ethyl]
benzyl}cyclobutyl)methyl]benzenesulfonamide;
N-[(1-{4-[2-(methylsulfonyl)ethyl]benzyl}cyclobutyl)methyl]naphthalene-1-sulfonamide;
N-({1-[4-(2-tert-butoxyethyl)benzyl]cyclopentyl}methyl)-
4-methylbenzenesulfonamide;
4-chloro-N-[(1-{4-[2-(pyrid-2-yloxy)ethyl]
benzyl}cyclopentyl)methyl]benzenesulfonamide;
N-({1-[4-(2-hydroxyethyl)benzyl]cyclopentyl}methyl)-4-
(methylsulfonyl)benzenesulfonamide;
4-chloro-N-({1-[4-(2-hydroxyethyl)benzyl]-3,3-
dimethylcyclobutyl}methyl)-benzenesulfonamide;
4-chloro-N-({1-[3-(2-hydroxyethyl)benzyl]
cyclopentyl}methyl)benzenesulfonamide;
2,4-dichloro-N-({1-[4-(2-hydroxyethyl)benzyl]
cyclopentyl}methyl)benzenesulfonamide;
4-chloro-N-({4-[4-(2-hydroxyethyl)benzyl]tetrahydro-2H-
pyran-4-yl}methyl)-benzenesulfonamide;
N-({1-[4-(2-hydroxyethyl)benzyl]cyclopentyl}methyl)
naphthalene-2-sulfonamide;
4-cyclohexyl-N-({1-[4-(2-hydroxyethyl)benzyl]
cyclopentyl}methyl)benzene-sulfonamide;
N-({1-[4-(2-hydroxyethyl)benzyl]cyclopentyl}methyl)pyridine-3-sulfonamide;
4-chloro-N-({1-[4-(2-hydroxyethyl)benzyl]
cyclopropyl}methyl)benzenesulfonamide;
4-chloro-N-({1-[4-(2-hydroxyethyl)benzyl]
cyclobutyl}methyl)benzenesulfonamide;
N-({1-[4-(2-hydroxyethyl)benzyl]cyclobutyl}methyl)-4-
methylbenzenesulfonamide;
2,3,4,5,6-pentafluoro-N-({1-[4-(2-hydroxyethyl)benzyl]
cyclopentyl}methyl)-benzenesulfonamide;
N-({1-[4-(2-hydroxyethyl)benzyl]cyclopentyl}methyl)-4-
methylbenzenesulfonamide;
N-({1-[4-(2-hydroxyethyl)benzyl]cyclopentyl}methyl)-4-
methylbenzenesulfonamide;
3,4,5-trifluoro-N-({1-[4-(2-hydroxyethyl)benzyl]
cyclopentyl}methyl)benzenesulfonamide;
3,5-dichloro-N-({1-[4-(2-hydroxyethyl)benzyl]
cyclopentyl}methyl)benzenesulfonamide;
N-({1-[4-(2-hydroxyethyl)benzyl]cyclopentyl}methyl)-3-
methylbenzenesulfonamide;
4-fluoro-N-({1-[4-(2-hydroxyethyl)benzyl]
cyclopentyl}methyl)benzenesulfonamide;
4-chloro-N-({1-[4-(2-hydroxyethyl)benzyl]
cyclopentyl}methyl)-3-(trifluoro-methyl)benzenesulfonamide;
N-({1-[4-(2-chloroethyl)benzyl]cyclobutyl}methyl)-2,3,4,
5,6-pentafluorobenzenesulfonamide;
N-({1-[4-(2-hydroxyethyl)benzyl]cyclopentyl}methyl)-4-
nitro-3-(trifluoro-methyl)benzenesulfonamide;
N-(cyclopropylmethyl)-N-({1-[4-(2-hydroxyethyl)benzyl]
cyclobutyl}methyl)-4-methylbenzenesulfonamide;
4-chloro-N-(cyclopropylmethyl)-N-({1-[4-(2-hydroxyethyl)
benzyl]cyclo-butyl}methyl)benzenesulfonamide;
and also the tautomeric, enantiomeric, diastereoisomeric and
epimeric forms, the esters and the pharmaceutically acceptable salts.

As compounds of the formula (I) according to the invention, preferred compounds are any compound chosen from:
2,4-dichloro-N-[(1-{4-[2-(cyclopropylmethoxy)ethyl]
benzyl}cyclobutyl)methyl]benzenesulfonamide
N-[(1-{4-[2-(cyclopropylmethoxy)ethyl]benzyl}cyclobutyl)
methyl]-4-methoxy-benzenesulfonamide
2,4-dichloro-N-[(1-{4-[2-(cyclopentylthio)ethyl]
benzyl}cyclobutyl)methyl]benzenesulfonamide
2,4-dichloro-N-[(1-{4-[2-(methylthio)ethyl]
benzyl}cyclobutyl)methyl]benzene sulfonamide
2,4-dichloro-N-[(1-{4-[2-(cyclopentylsulfonyl)ethyl]
benzyl}cyclobutyl)methyl]-benzenesulfonamide
2,4-dichloro-N-[(1-{4-[2-(methylsulfonyl)ethyl]
benzyl}cyclobutyl)methyl]benzenesulfonamide
N-[(1-{4-[2-(methylsulfonyl)ethyl]benzyl}cyclobutyl)methyl]naphthalene-1-sulfonamide
N-({1-[4-(2-hydroxyethyl)benzyl]cyclopentyl}methyl)-4-
(methylsulfonyl)benzenesulfonamide 2,4-dichloro-N-({1-[4-(2-hydroxyethyl)benzyl]
cyclopentyl}methyl)benzene-sulfonamide
N-({1-[4-(2-hydroxyethyl)benzyl]cyclopentyl}methyl)
naphthalene-2-sulfonamide
4-chloro-N-({1-[4-(2-hydroxyethyl)benzyl]
cyclobutyl}methyl)benzenesulfonamide
N-({1-[4-(2-hydroxyethyl)benzyl]cyclobutyl}methyl)-4-
methylbenzenesulfonamide
2,3,4,5,6-pentafluoro-N-({1-[4-(2-hydroxyethyl)benzyl]
cyclopentyl}methyl)-benzenesulfonamide
N-({1-[4-(2-hydroxyethyl)benzyl]cyclopentyl}methyl)-4-
methylbenzenesulfonamide
3,4,5-trifluoro-N-({1-[4-(2-hydroxyethyl)benzyl]
cyclopentyl}methyl)benzenesulfonamide
3,5-dichloro-N-({1-[4-(2-hydroxyethyl)benzyl]
cyclopentyl}methyl)benzenesulfonamide
N-({1-[4-(2-hydroxyethyl)benzyl]cyclopentyl}methyl)-3-
methylbenzenesulfonamide
4-chloro-N-({1-[4-(2-hydroxyethyl)benzyl]
cyclopentyl}methyl)-3-(trifluoro-methyl)benzene-
sulfonamide
N-({1-[4-(2-chloroethyl)benzyl]cyclobutyl}methyl)-2,3,4,
5,6-pentafluorobenzenesulfonamide,
2,3,4,5,6-pentafluoro-N-[(1-{4-[2-(tetrahydro-2H-pyran-2-
yloxy)ethyl]benzyl}-cyclopentyl)methyl]benzene-
sulfonamide;
4-nitro-N-[(1-{4-[2-(tetrahydro-2H-pyran-2-yloxy)ethyl]
benzyl}cyclopentyl)-methyl]benzenesulfonamide;
4-cyclohexyl-N-[(1-{4-[2-(tetrahydro-2H-pyran-2-yloxy)
ethyl]benzyl}cyclo-pentyl)methyl]benzenesulfonamide;
N-[(1-{4-[2-(tetrahydro-2H-pyran-2-yloxy)ethyl]
benzyl}cyclopentyl)methyl]-naphthalene-2-sulfonamide,
and also the tautomeric, enantiomeric, diastereoisomeric and epimeric forms, the esters and the pharmaceutically acceptable salts.

Preferably, the retinopathy is diabetic retinopathy. Even more preferentially, the retinopathy is in its early stage.

According to another aspect, the present invention also relates to the use of a compound of the formula (I) for the preparation of a medicament for specifically inhibiting caspase-10 in a patient in need thereof, preferably newly diagnosed diabetic patients and/or patients suffering from early retinopathy.

According to another preferred aspect, the said medicament is suitable for the prevention of and/or treating the microvascular complications of diabetes, preferably retinopathy.

According to the present invention, the alkyl radicals represent saturated hydrocarbon-based radicals, in a straight or branched chain, of 1 to 20 carbon atoms and preferably of 1 to 5 carbon atoms.

If they are linear, mention may be made especially of methyl, ethyl, propyl, butyl, pentyl, hexyl, octyl, nonyl, decyl, dodecyl, hexadecyl and octadecyl radicals.

If they are branched or substituted by one or more alkyl radicals, mention may be made especially of isopropyl, tert-butyl, 2-ethylhexyl, 2-methylbutyl, 2-methylpentyl, 1-methylpentyl and 3-methylheptyl radicals.

The term "perhaloalkyl" means alkyl groups in which all the hydrogen atoms are replaced with a halogen atom. The —$CF_3$ radical is especially preferred.

The alkoxy radicals according to the present invention are radicals of the formula —O-alkyl, the alkyl being as defined above. Similarly, the term "perhalogenated —O-alkyl" or "—O-perhaloalkyl" means an alkoxy group in which all the hydrogens of the alkyl group have been replaced with a halogen atom; the —$OCF_3$ group is especially preferred.

Among the Halogen atoms that are more particularly mentioned are fluorine, chlorine, bromine and iodine atoms, preferably fluorine.

The alkenyl radicals represent hydrocarbon-based radicals in a straight or linear chain, and comprise one or more ethylenic unsaturations. Among the alkenyl radicals that may especially be mentioned are allyl or vinyl radicals.

The alkynyl radicals represent hydrocarbon-based radicals, in a straight or linear chain, and comprise one or more acetylenic unsaturations. Among the alkynyl radicals, mention may be made especially of acetylene.

The cycloalkyl radical is a saturated or partially unsaturated, non-aromatic mono-, bi- or tricyclic hydrocarbon-based group of 3 to 10 carbon atoms, especially, such as cyclopropyl, cyclopentyl, cyclohexyl or adamantyl, and also the corresponding rings containing one or more unsaturations.

Aryl or Ar denotes a monocyclic or bicyclic hydrocarbon-based aromatic system of 6 to 10 carbon atoms.

Among the aryl radicals that may especially be mentioned are phenyl and naphthyl radicals.

Among the -alkylaryl radicals, mention may be made especially of benzyl and phenethyl radicals.

Het denotes a heteroaryl group; the heteroaryl radicals denote monocyclic or bicyclic aromatic systems of 5 to 10 carbon atoms, comprising one or more hetero atoms chosen from nitrogen, oxygen and sulfur. Among the heteroaryl radicals that may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]-pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl and carbazolyl, and also the corresponding groups derived from their fusion or from fusion with the phenyl nucleus. The preferred heteroaryl groups comprise thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl and thiadiazolyl, and groups derived from fusion with a phenyl nucleus, and more particularly quinolinyl, carbazolyl and thiadiazolyl.

The heterocyclyl radicals denote saturated or partially unsaturated non-aromatic monocyclic or bicyclic systems of 5 to 10 carbon atoms, comprising one or more hetero atoms chosen from N, O and S. Among the heterocyclyl groups, mention may be made especially of epoxyethyl, oxiranyl, aziridinyl, tetrahydrofuranyl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetra-hydrothiopyranyl, dithianyl, thiomorpholinyl, dihydrofuranyl, 2-imidazolinyl, 2,3-pyrolinyl, pyrazolinyl, dihydrothiophenyl, dihydropyranyl, pyranyl, tetrahydropyridyl, dihydropyridyl, tetrahydropyrinidinyl and dihydrothiopyranyl, and the corresponding groups derived from fusion with a phenyl nucleus, and more particularly epoxyethyl, oxiranyl, tetrahydrofuranyl, dioxolanyl, pyrrolidinyl, tetrahydropyranyl, dioxanyl, morpholinyl, piperidyl, piperazinyl, and tetrahydrothiopyranyl rings, and more particularly the tetrahydropyranyl ring.

The expression "pharmaceutically acceptable salts" refers to the relatively non-toxic mineral and organic acid-addition salts, and the base-addition salts, of the compounds of the present invention. These salts can be prepared in situ during the final isolation and purification of the compounds. In particular, the acid-addition salts can be prepared by separately reacting the purified compound in its purified form with an organic or mineral acid and isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxynaphthoates, gentisic acid, isethionates, di-p-toluoyltartrates, methanesulfonates, ethane-sulfonates, benzenesulfonates, p-toluenesulfonates, cyclohexyl sulfamates and quinates-laurylsulfonate, and analogues. (See for example S. M. Berge et al. "Pharmaceutical Salts" *J. Pharm. Sci*, 66: pp. 1-19 (1977) which is incorporated herein by reference). The acid-addition salts can also be prepared by separately reacting the purified compound in its acid form with an organic or mineral base and isolating the salt thus formed. The acid-addition salts include amine salts and metal salts. The suitable metal salts include the sodium, potassium, calcium, barium, zinc, magnesium and aluminium salts. The sodium and potassium salts are preferred. The suitable mineral base-addition salts are prepared from metallic bases including sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

The term "precursor group" means any chemical function allowing the desired chemical function to be formed by means of one or more suitable chemical reactions referred to herein as "derivatisation reactions".

The invention also relates to the tautomeric forms, enantiomers, diastereoisomers, epimers and organic or mineral salts of the compounds of the general formula (I).

The compounds of the invention of the formula (I) as defined above containing a sufficiently acidic function or a sufficiently basic function, or both, may include the corresponding pharmaceutically acceptable salts of an organic or mineral acid or of an organic or mineral base.

The compounds of the general formulae (I) can be prepared by application or adaptation of any method known per se and/or within the capacity of a person skilled in the art, especially those described by Larock in *Comprehensive Organic Transformations*, VCH Pub., 1989, or by application or adaptation of the processes described in the examples that follow.

According to another subject, the present invention also relates to the process for the preparation of the compounds of the formula (I) as defined above.

It is understood that the compounds of the formula (I) can be prepared via a similar process, starting with suitable starting materials.

According to the invention, the process for the preparation of a compound of the formula (I) includes the step of preparing a corresponding compound of the formula (I'):

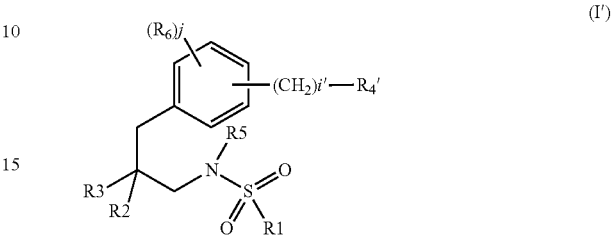

in which R2, R3, R6 and j are as defined in formula (I), i' represents 0 or i as defined in formula (I) and R4' represents a hydrogen atom, or represents R4 as defined in formula (I) or represents a group -Z-Gp in which Gp represents a leaving group, or alternatively represents a —CO$_2$H group, starting with a compound of the formula (III):

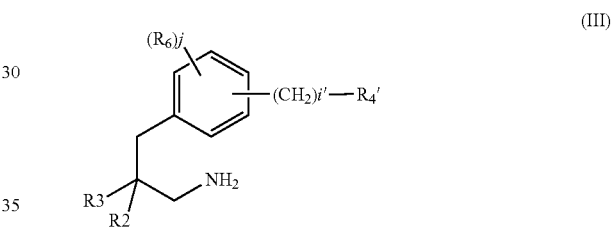

via the action of a compound of the formula (IV):

R1-SO$_2$-Hal  (IV)

in which R1 is as defined in formula (I) and Hal represents a halogen atom, preferably chlorine, optionally followed, if R5 is other than H in formula (I'), by alkylation of the nitrogen atom.

Preferably, the process is performed in the presence of a base, especially an organic base, such as triethylamine, or pyridine or 4-dimethylaminopyridine alone or as a mixture with triethylamine, or alternatively mineral bases, such as K$_2$CO$_3$ or KOH, in a suitable solvent medium, such as dichloromethane or THF, DMF or pyridine, or water preferably used with the abovementioned mineral bases.

The process is generally performed at room temperature, and it may occasionally be preferable to start the reaction at a temperature of less than or equal to 0° C. or at elevated temperature (especially, in the latter case, if the process is performed in the presence of K$_2$CO$_3$/water, pyridine).

If, in formula (I'), i' represents i as defined in formula (I) and R4' represents a group -Z-(alkyl)n-Tp in which n=p=0, i.e. a group -ZH, the compound of the formula (I) in which n and/or p is (are) other than 0, can be obtained from compound (I') via alkylation of the group -ZH. The process can especially be performed via the action of a compound of the formula Hal-(alkyl)n-Tp, in which alkyl, n, T and p are as defined in formula (I) and Hal represents a halogen atom, preferably chlorine. The process is generally performed in a microwave oven.

The process can also be performed using a compound of the formula $Cl_3C—C(=NH)—O\leq(alkyl)n-Tp$, in which alkyl, n, T and p are as defined in formula (I), or a similar compound. The process is generally performed in the presence of $BF_3-Et_2O$, or a suitable Lewis acid in a suitable solvent medium, such as THF or ether.

If, in formula (I'), i' represents i as defined in formula (I) and R4' represents a group -Z-Gp, in which Gp represents a leaving group, such as the -THP group or a silyl group, the compound of the formula (I) in which R4 represents a group -Z-(alkyl)n-Tp in which n=p=0 can be obtained from compound (I') via removal of the leaving group. The process can especially be performed by passing through resin, such as Dowex resin, eluting with methanol, THF or dichloromethane.

If, in formula (I'), i' represents i as defined in formula (I) and R4' represents a —$CO_2H$ group, the compound of the formula (I) in which R4 represents a group -Z-(alkyl)n-Tp in which n=p=0 can be obtained from compound (I') via reduction of the —$CO_2H$ group. The process can be especially performed using $BH_3.Me_2S$ or $LiAlH_4$ dissolved in toluene, THF or ether.

If, in formula (I'), R5 represents a hydrogen atom, the compound of the formula (I) can be obtained from compound (I') via alkylation of the —NH— group.

The process can especially be performed via the action of a compound of the formula Hal-R5, in which R5 is as defined in formula (I) and Hal represents a halogen atom.

The process is generally performed using a base, especially t-BuOK, KOH or NaH.

If, in formula (I'), i' represents i as defined in formula (I) and R4' represents a group -Z-(alkyl)n-Tp in which n, p, alkyl and T are as defined in formula (I) and Z represents —S(O)q— in which q=0, the compound of the formula (I) in which q is other than 0 can be obtained via oxidation of the compound of the formula (I').

The process can especially be performed via the action of any suitable oxidising agent for a sulfur function, such as mCPBA, or alternatively by means of hydrogen peroxide in a solvent medium, such as dichloromethane, acetic acid or acetone.

The process according to the invention can also include the step of isolating the compound (I) formed.

The compound of the formula (III) can be obtained from the compound of the corresponding formula (V):

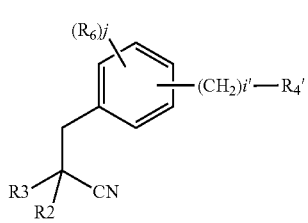

(V)

in which R2, R3, R6 and j are as defined in formula (I), and i' and R4' are as defined in formula (I'), via reduction of the nitrile function using any suitable reducing agent. The process can especially be performed using $BH_3.Me_2S$ or $LiAlH_4$ dissolved in toluene, THF or ether.

The compound of the formula (V) can be obtained from the compound of the corresponding formula (VI):

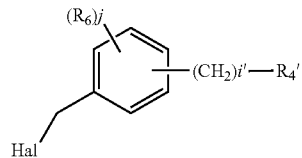

(VI)

in which R6 and j are as defined in formula (I), i' and R4' are as defined in formula (I') and Hal represents a halogen atom, such as chlorine or bromine, via the action of a compound of the formula (VII):

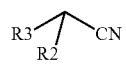

(VII)

in which R2 and R3 are as defined in formula (I').

The process is generally performed using lithium diisopropylamide (LDA) in the presence of hexamethylphosphotriamide (HMPT) or dimethylimidazolidinone in a solvent, such as THF, ether or dioxane.

The compound of the formula (VI) is commercially available or can be prepared via application or adaptation of methods known to those skilled in the art using suitable starting materials, or alternatively via application or adaptation of the methods described in the examples.

Similarly, the products of the formulae (IV) and (VII) are commercially available or can be prepared via application or adaptation of methods known to those skilled in the art using suitable starting materials.

The base products or the reagents used are commercially available and/or can be prepared via application or adaptation of known processes, for example processes as described in the Reference Examples or obvious chemical equivalents thereof.

In the reactions described hereinabove, it may be necessary to protect reactive functional groups, for example the hydroxyl, amino, imino, thio or carboxyl groups, if they are desired in the final product, to avoid their unwanted participation in the reactions. The conventional protecting groups can be used in accordance with the standard practice; for examples, see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The compound of the formula (I) thus prepared can be recovered from the reaction mixture via the conventional means. For example, the compounds can be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product can also be purified, if so desired, by various techniques, such as recrystallisation, reprecipitation or various chromatographic techniques, especially column chromatography or preparative thin-layer chromatography.

It will be appreciated that the compounds that are useful according to the present invention may contain asymmetric centres. These asymmetric centres can be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (I) above. Isomers of this type can be separated from their mixtures by application or adaptation of known processes, for example chromatography techniques or recrystallisation techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention can be prepared by reacting the free base with the appropriate acid, by application or adaptation of known processes. For example, the acid-addition salts of the compounds that are useful according to the present invention can be prepared either by dissolving the free base in water or in a basified aqueous solution or suitable solvents comprising the appropriate acid, and isolating the solvent by evaporating the solution, or by reacting the free base and the acid in an organic solvent, in which case the salt separates out directly or can be obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention can be regenerated from the salts by application or adaptation of known processes. For example, the parent compounds that are useful according to the invention can be regenerated from their acid-addition salts by treatment with an alkali, for example aqueous sodium bicarbonate solution or aqueous ammonia solution.

The compounds that are useful according to the present invention can be regenerated from their base-addition salts by application or adaptation of known processes. For example, the parent compounds that are useful according to the invention can be regenerated from their base-addition salts by treatment with an acid, for example hydrochloric acid.

The base-addition salts may be formed if the compound that is useful according to the invention contains a carboxyl group, or a sufficiently acidic bioisostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide and the like.

The compounds that are useful according to the present invention can be readily prepared, or formed during the process of the invention, in the form of solvates (for example hydrates). The hydrates of the compounds that are useful according to the present invention can be readily prepared by recrystallisation of an aqueous/organic solvent mixture, using organic solvents, such as dioxane, tetrahydrofuran or methanol.

According to another subject, the present invention also relates to pharmaceutical compositions comprising a compound of the general formula (I) as defined above and pharmaceutically acceptable excipient.

Preferably, the said composition comprises an effective amount of the compound according to the invention.

Preferably, the said composition is administered to a patient in need thereof.

The pharmaceutical compositions according to the invention can be presented in forms intended for parenteral, oral, rectal, permucous or percutaneous administration.

They will thus be presented in the form of injectable solutions or suspensions or multi-dose bottles, in the form of plain or coated tablets, sugar-coated tablets, wafer capsules, gel capsules, pills, sachets, powders, suppositories or rectal capsules, solutions or suspensions, for percutaneous use in a polar solvent, or for permucous use.

The excipients that are suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most appropriately used.

The dosage may vary within wide ranges (0.5 mg to 1000 mg) depending on the therapeutic indication and the route of administration, and also on the age and weight of the patient.

The examples that follow are given as non-limiting illustrations of the present invention. The starting materials are commercially available or can be prepared via processes that are known per se.

The frequency of the NMR machine used to record the proton spectra of the examples given below is 300 MHz. The abbreviation s denotes a singlet; d a doublet; t a triplet; q a quartet and m a multiplet. The values are expressed in ppm.

The LC-MS spectra are obtained on a simple quadrupole machine equipped with an electrospray probe.

The reaction schemes below are given as non-limiting illustrations of the process according to the invention:

EXAMPLES 1 TO 20
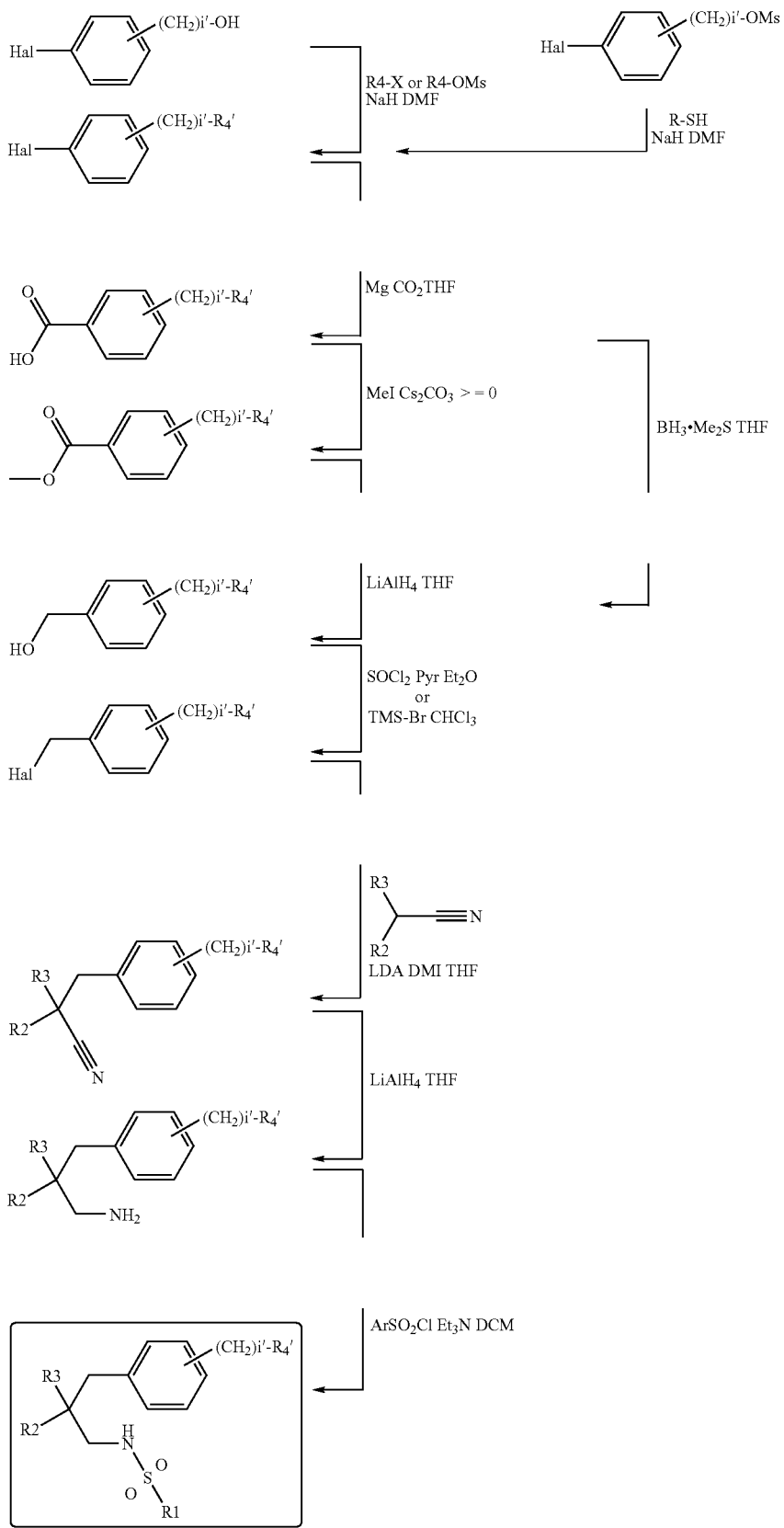

EXAMPLES 21 TO 30
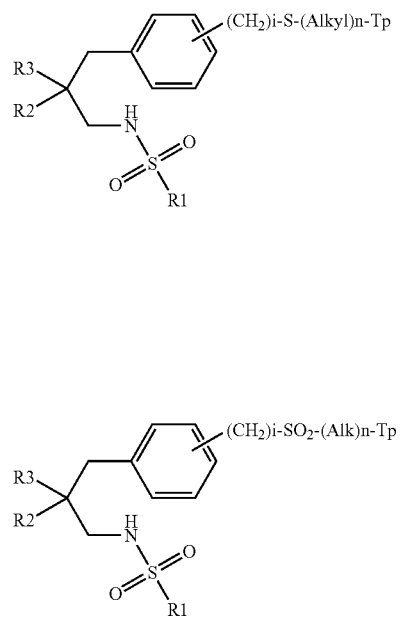
EXAMPLES 31-32 AND 70-71
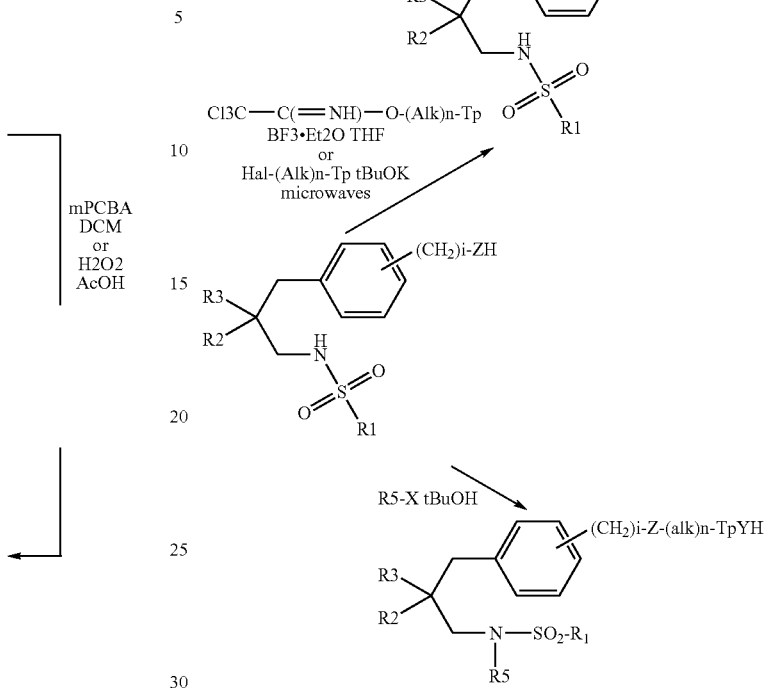
EXAMPLES 33-69
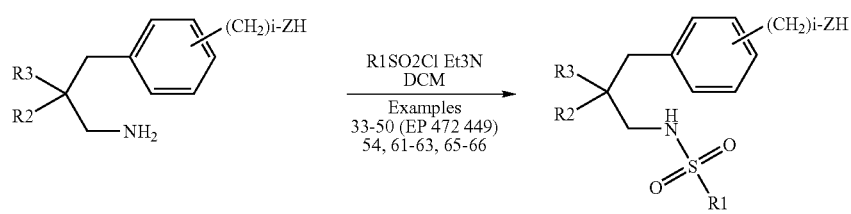

EXAMPLES 72-73

To be Deleted if FG is not Modified so as to Include Examples 72 and

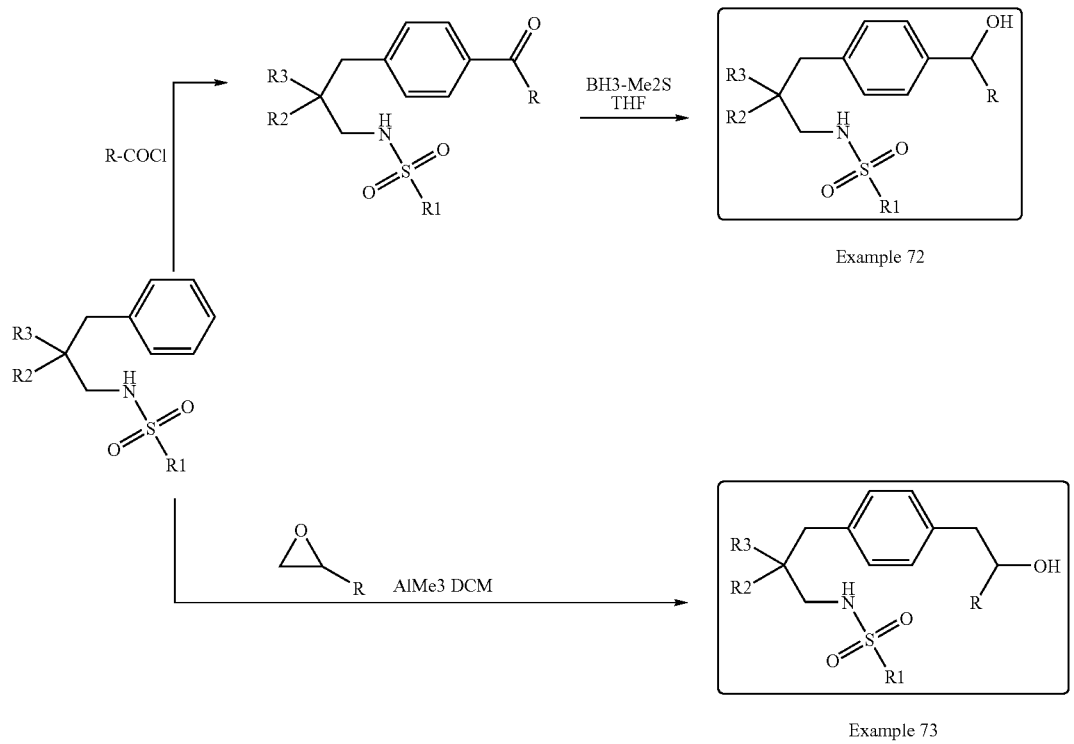

Example 72

Example 73

1.1 EXAMPLE 1

2,4-Dichloro-N-[(1-{4-[2-(cyclopropylmethoxy)ethyl]benzyl}cyclobutyl)methyl]benzenesulfonamide a) 1-Bromo-4-[2-(cyclopropylmethoxy)ethyl]benzene

To a suspension under nitrogen of 656.5 mg (16.4 mmol) of NaH (at 60% in oil) in 15 ml of DMF is added over 10 minutes a solution of 3 g (14.9 mmol) of 2-(4-bromophenyl)ethanol in 5 ml of DMF. After stirring for 30 minutes at room temperature, the reaction medium is cooled to 10° C. and a solution of 2.4 g (17.9 mmol) of (bromomethyl)cyclopropane in 10 ml of DMF is added over 15 minutes.

After stirring for 16 hours at room temperature, the reaction medium is poured into ice-cold water and extracted with ethyl acetate. The organic phase is washed with water, dried over $Na_2SO_4$ and concentrated under vacuum to give an oil. After purification by flash chromatography on silica gel in a dichloromethane/heptane mixture (4/1), 1.94 g of the expected compound are obtained.

Yield: 51.0%

NMR ($CDCl_3$): 0.2 (m, 2H), 0.5 (m, 2H), 1.0 (m, 1H), 2.8 (t, J=7.2 Hz, 2 H), 3.3 (d, J=6.7 Hz, 2H), 3.6 (t, J=7.2 Hz, 2H), 7.1 (m, 2H), 7.4 (m, 2 H)

b) 4-[2-(Cyclopropylmethoxy)ethyl]benzoic acid

A solution of 949.2 mg (3.7 mmol) of the compound prepared in Example 1a, in 3 ml of THF, is added dropwise to a mixture under nitrogen composed of 90.5 mg (3.7 mmol) of magnesium filings, 2 ml of THF and a crystal of iodine. The reaction medium is then maintained at reflux for 1 hour, until the magnesium has disappeared. After cooling to room temperature, the reaction medium is poured onto 10 g of crushed cardice.

The mixture is allowed to warm to room temperature with stirring, followed by addition of 50 ml of ethyl ether, and is acidified with 16% HCl. The recovered organic phase is washed with water and then extracted with 3×10 ml of 1N NaOH solution.

The basic aqueous phase is acidified with 16% HCl to give a white precipitate, which is washed with water. After drying under vacuum, 417 mg of a white solid are obtained.

Yield: 50.9%

NMR (DMSO-$d_6$): 0.1 (m, 2H), 0.4 (m, 2H), 0.9 (m, 1H), 2.9 (t, J=6.8 Hz, 2H), 3.2 (d, J=6.9 Hz, 2H), 3.6 (t, J=6.8 Hz, 2H), 7.4 (m, J=8.2 Hz, 2H), 7.9 (m, 2 H), 12.8 (s, 1H.)

c) {4-[2-(Cyclopropylmethoxy)ethyl]phenyl}methanol

To a solution under nitrogen of 410 mg (1.9 mmol) of the compound prepared in Example 1b, in 100 ml of THF, are added 1.024 ml (2 mmol) of $BH_3.Me_2S$ (2 M solution in toluene). After stirring for two hours at room temperature, 39.5 ml of water, 89.5 ml of toluene and 283 mg (1.1 equivalents) of $K_2CO_3$ dissolved in 39.5 ml of water are added. After separation of the phases by settling, the organic phase is recovered and the aqueous phase is extracted with 80 ml of toluene. The combined organic phases are washed with water, dried over Na₂SO₄ and concentrated under vacuum to give 299 mg of a yellow oil. This oil is taken up in 35 ml of methanol and stirred for one hour at room temperature.

After removal of the supernatant and concentration of the residue under vacuum, 258 mg of oil are obtained.

Yield: 67.0%

NMR (CDCl₃): 0.2 (m, 2H), 0.5 (m, 2H), 1.1 (m, 1H), 1.6 (s, 1H), 2.9 (t, J=7.3 Hz, 2H), 3.3 (d, J=6.9 Hz, 2H), 3.6 (t, J=7.3 Hz, 2H), 4.7 (s, 2 H), 7.3 (m, 4H)

d) 1-(Chloromethyl)-4-[2-(cyclopropylmethoxy)ethyl]benzene

To a mixture of 256 mg (1.24 mmol) of the compound prepared in Example 1c, 0.12 ml (1.49 mmol) of pyridine and 5 ml of ethyl ether is added, at 0° C., 0.108 ml (1.49 mmol) of thionyl chloride. After stirring for 30 minutes at 0° C., the mixture is allowed to warm to room temperature.

After stirring for 16 hours, 10 ml of water are added and the mixture is extracted with ether. The organic phase is washed with water, dried over Na₂SO₄ and concentrated under vacuum to give 248 mg of a yellow oil.

Yield: 89.0%

NMR (CDCl₃): 0.2 (m, 2H), 0.5 (m, 2H), 1.1 (m, 1H), 2.9 (t, J=7.3 Hz, 2 H), 3.3 (d, J=6.9 Hz, 2H), 3.6 (t, J=7.3 Hz, 2H), 4.6 (s, 2H), 7.3 (m, 4H)

e) 1-{4-[2-(Cyclopropylmethoxy)ethyl]benzyl}cyclobutanecarbonitrile

To a solution under nitrogen of 0.169 ml (1.2 mmol) of diisopropylamine in 2.5 ml of THF, maintained at −30° C., is added 0.75 ml (1.2 mmol) of n-butyllithium (1.6 M solution in hexane) over 10 minutes. After stirring for 15 minutes at −30° C., 0.172 ml (1.57 mmol) of 1,3-dimethyl-2-imidazolidinone is added, at −60° C., over 15 minutes. Next, 88.43 mg (1.09 mmol) of cyclobutanecarbonitrile dissolved in 0.75 ml of THF are added over 10 minutes, at −70° C. The orange solution obtained is stirred for one hour at −70° C., after which 245 mg (1.09 mmol) of the compound prepared in Example 1d dissolved in 0.75 ml of THF are added over 10 minutes. After stirring for 2 hours at −70° C., the orange reaction medium is poured into 15 ml of water, acidified with 1N HCl and extracted with ethyl ether. The organic phase is washed with water, dried over Na₂SO₄ and concentrated under vacuum to give a yellow oil. After purification by flash chromatography on silica gel, in dichloromethane, 141 mg of a pale yellow oil are obtained.

Yield: 48.0%

NMR (CDCl₃): 0.2 (m, 2H), 0.5 (m, 2H), 1.1 (m, 1H), 2.1 (m, 4H), 2.5 (m, 2H), 2.9 (t, J=7.4 Hz, 2H), 3.0 (s, 2H), 3.3 (d, J=6.9 Hz, 2H), 3.6 (t, J=7.4 Hz, 2 H), 7.2 (m, 4H)

f) [(1-{4-[2-(Cyclopropylmethoxy)ethyl]benzyl}cyclobutyl)methyl]amine

To a suspension under nitrogen of 49.31 mg (1.3 mmol) of LiAlH₄ in 3 ml of THF are added 140 mg (0.52 mmol) of the compound prepared in Example 1e dissolved in 2 ml of THF. After stirring for 4 hours at reflux, the excess hydride is destroyed with water, and 10 ml of ethyl ether and 2 g of Na₂SO₄ are added. After filtering and concentrating under vacuum, the residue is taken up in 15 ml of water, acidified with 16% HCl, washed with ethyl ether and then brought to pH 10 with NaOH solution. This aqueous phase is extracted with ether.

The organic phase washed with water is dried over Na₂SO₄ and concentrated under vacuum to give 96.8 mg of a colourless oil, which is used without purification.

Yield: 87.0%

NMR (CDCl₃): 0.0 (m, 2H), 0.3 (m, 2H), 0.9 (m, 1H), 1.7 (m, 8H), 2.5 (s, 2 H), 2.6 (s, 2H), 2.7 (t, J=7.4 Hz, 2H), 3.1 (d, J=6.9 Hz, 2H), 3.5 (t, J=7.4 Hz, 2H), 6.9 (m, 4H)

g) 2,4-Dichloro-N-[(1-{4-[2-(cyclopropylmethoxy)ethyl]benzyl}cyclobutyl)-methyl]benzenesulfonamide To a solution of 96.8 mg (0.31 mmol) of the compound prepared in Example 1f, in 1 ml of dichloromethane, is added 0.129 ml (0.92 mmol) of triethylamine, followed by addition over five minutes, at −20° C., of a solution of 83.184 mg (0.34 mmol) of 2,4-dichlorobenzenesulfonyl chloride in 0.5 ml of dichloromethane. After stirring for 30 minutes at −20° C. and for 3 hours at room temperature, the reaction medium is poured into 10 ml of water and extracted with dichloromethane.

The organic phase, washed with water and dried over Na₂SO₄, is concentrated under vacuum to give a pasty solid, which is purified by flash chromatography on silica gel in chloroform. 98 mg of an off-white solid are obtained.

Yield: 66.0%

NMR (CDCl₃): 0.2 (m, 2H), 0.5 (m, 2H), 1.1 (m, 1H), 1.8 (m, 6H), 2.7 (s, 2H), 2.8 (d, J=6.4 Hz, 2H), 2.9 (t, J=7.3 Hz, 2H), 3.3 (d, J=6.9 Hz, 2 H), 3.6 (t, J=7.3 Hz, 2H), 4.8 (t, J=6.4 Hz, 1H), 7.0 (d, J=8.0 Hz, 2H), 7.1 (m, 2 H), 7.4 (dd, J=8.5, 2.0 Hz, 1H), 7.5 (d, J=1.9 Hz, 1H), 8.0 (d, J=8.6 Hz, 1H)

LC-MS: ES+ 482.3 484.3 486.3 2 chlorine atoms

1.2 EXAMPLES 2-5

Obtained by working as in Example 1.

TABLE 1

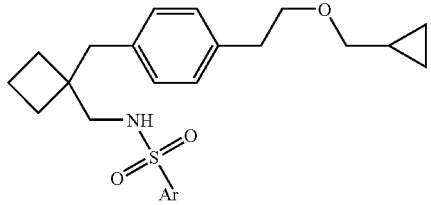

| Ex | Ar | NMR | LC-MS |
| --- | --- | --- | --- |
| 2 | 4-Chlorophenyl | 0.2 (m, 2H), 0.5 (m, 2H), 1.1 (m, 1H), 1.8 (m, 6H), 2.7 (s, 2H), 2.9 (m, 4H), 3.3 (d, J = 6.9 Hz, 2H), 3.6 (t, J = 7.3 Hz, 2H), 4.3 (t, J = 6.3 Hz, 1H), 7.0 (d, J = 8.0 Hz, 2H), 7.1 (m, 2H), 7.5 (m, 2H), 7.7 (m, 2H) | ES+ 470.3 472.3 1 chlorine atom |

TABLE 1-continued

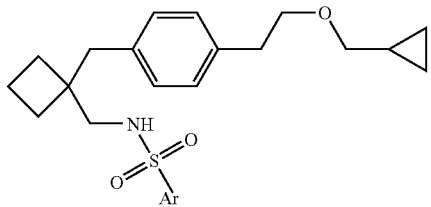

| Ex | Ar | NMR | LC-MS |
|---|---|---|---|
| 3 | 4-Methylphenyl | 0.2 (m, 2H), 0.5 (m, 2H), 1.1 (m, 1H), 1.8 (m, 6H), 2.4 (s, 3H), 2.7 (s, 2H), 2.9 (m, 4H), 3.3 (d, J = 6.9 Hz, 2H), 3.6 (t, J = 7.4 Hz, 2H), 4.2 (t, J = 6.3 Hz, 1H), 7.0 (d, J = 7.8 Hz, 2H), 7.1 (d, J = 7.8 Hz, 2H), 7.3 (m, 2H), 7.7 (d, J = 8.2 Hz, 2H) | ES+ 428.4 450.4 |
| 4 | 1-Naphthyl | 0.2 (m, 2H), 0.5 (m, 2H), 1.1 (m, 1H), 1.7 (m, 6H), 2.6 (s, 2H), 2.8 (m, 4H), 3.3 (d, J = 6.9 Hz, 2H), 3.6 (m, 2H), 4.4 (t, J = 6.4 Hz, 1H), 6.8 (d, J = 8.0 Hz, 2H), 6.9 (d, J = 8.0 Hz, 2H), 7.5 (m, 1H), 7.7 (m, 2H), 8.0 (m, 1H), 8.1 (d, J = 8.2 Hz, 1H), 8.2 (dd, J = 7.3, 1.2 Hz, 1H), 8.6 (d, J = 8.6 Hz, 1H) | ES+ 464.4 486.4 |
| 5 | 4-Methoxyphenyl | 0.2 (m, 2H), 0.5 (m, 2H), 1.1 (m, 1H), 1.8 (m, 6H), 2.7 (s, 2H), 2.9 (m, 4H), 3.3 (d, J = 6.9 Hz, 2H), 3.6 (t, J = 7.4 Hz, 2H), 3.9 (s, 3H), 4.1 (t, J = 6.5 Hz, 1H), 7.0 (m, 4H), 7.1 (m, 2H), 7.8 (m, 2H) | ES+ 444.4 |

1.3 EXAMPLE 6

4-Chloro-N-[(1-{4-[2-(cyclopentyloxy)ethyl]benzyl}cyclobutyl)methyl]benzenesulfonamide a) 1-Bromo-4-[2-(cyclopentyloxy)ethyl]benzene Obtained by working as in Example 1a, starting with cyclopentylmethane sulfonate (J. Am. Chem. Soc. (1997) 119, 2125).
Yield: 36%
NMR (CDCl$_3$): 1.6 (m, 8H), 2.8 (t, J=7.1 Hz, 2H), 3.5 (t, J=7.1 Hz, 2H), 3.9 (m, 1H), 7.1 (m, 2H), 7.4 (m, 2H)

b) 4-[2-(Cyclopentyloxy)ethyl]benzoic acid

Obtained by working as in Example 1b, starting with the compound obtained in Example 6a.
Yield: 60.0%
NMR (DMSO-d$_6$): 1.5 (m, 8H), 2.8 (t, J=6.9 Hz, 2H), 3.5 (t, J=6.9 Hz, 2H), 3.8 (m, 1H), 7.3 (d, J=8.4 Hz, 2H), 7.8 (m, 2H), 12.8 (s, 1H)

c) Methyl 4-[2-(cyclopentyloxy)ethyl]benzoate

A mixture of 2.97 g (12.68 mmol) of the compound obtained in Example 6b, 8.26 g (25.35 mmol) of caesium carbonate and 50 ml of acetone is stirred for 30 minutes at room temperature, followed by addition of 1.578 ml (25.35 mmol) of methyl iodide. After stirring for 16 hours, the reaction medium is concentrated under vacuum, taken up in ethyl ether, washed with water and dried over Na$_2$SO$_4$.
After concentrating under vacuum, 2.95 g of a yellow oil are obtained.
Yield: 94%
NMR (CDCl$_3$): 1.6 (m, 8H), 2.9 (t, J=7.1 Hz, 2H), 3.6 (t, J=7.1 Hz, 2H), 3.9 (m, 1H), 3.9 (s, 3H), 7.3 (m, 2H), 7.9 (m, 2H)

d) {4-[2-(Cyclopentyloxy)ethyl]phenyl}methanol

To a suspension of 1.353 g (35.64 mmol) of LiAlH$_4$ in 60 ml of THF, under nitrogen, are added 2.95 g (11.88 mmol) of the compound prepared in Example 6c dissolved in 15 ml of THF. The reaction medium is refluxed for 3.5 hours. After cooling, 10 ml of water are added dropwise, followed by addition of 100 ml of ethyl ether. The precipitate formed is filtered off. The filtrate is dried over Na$_2$SO$_4$ and then concentrated under vacuum to give an oil, which is purified by flash chromatography on silica gel in dichloromethane. 1.92 g of oil are obtained.
Yield: 73%
NMR (CDCl$_3$): 1.5 (m, 9H), 2.8 (t, J=7.3 Hz, 2H), 3.5 (t, J=7.3 Hz, 2H), 3.8 (m, 1H), 4.6 (s, 2H), 7.2 (m, 4H)

e) 1-(Bromomethyl)-4-[2-(cyclopentyloxy)ethyl]benzene

To a solution of 1.92 g (8.715 mmol) of the compound obtained in Example 6d, in 28 ml of chloroform, are added 1.725 g (13.07 mmol) of trimethylsilyl bromide dissolved in 8 ml of chloroform. After stirring for one hour at room temperature, 60 ml of dichloromethane are added and the mixture is washed with water and then dried over Na$_2$SO$_4$. After concentrating under vacuum, 2.39 g of a yellow oil are obtained, which oil is purified by flash chromatography on silica gel in dichloromethane. 2.21 g of oil are obtained.
Yield: 90%
NMR (CDCl$_3$): 1.6 (m, 8H), 2.8 (t, J=7.3 Hz, 2H), 3.5 (t, J=7.3 Hz, 2H), 3.8 (m, 1H), 4.4 (s, 2H), 7.2 (m, 4H)

f) 1-{4-[2-(Cyclopentyloxy)ethyl]benzyl}cyclobutanecarbonitrile

Obtained by working as in Example 1e.
Yield: 32%
NMR (CDCl$_3$): 1.6 (m, 8H), 2.1 (m, 4H), 2.5 (m, 2H), 2.8 (t, J=7.3 Hz, 2H), 3.0 (s, 2H), 3.6 (t, J=7.3 Hz, 2H), 3.9 (m, 1H), 7.2 (m, 4H)

g) [(1-{4-[2-(Cyclopentyloxy)ethyl]benzyl}cyclobutyl)methyl]amine

Obtained by working as in Example 1f.
Yield: 48%
NMR (CDCl$_3$): 1.7 (m, 16H), 2.6 (s, 2H), 2.7 (s, 2H), 2.8 (t, J=7.5 Hz, 2H), 3.6 (t, J=7.5 Hz, 2H), 3.9 (m, 1H), 7.1 (m, 4H)

h) 4-Chloro-N-[(1-{4-[2-(cyclopentyloxy)ethyl]benzyl}cyclobutyl)methyl]benzenesulfonamide Obtained by working as in Example 1g, starting with 4-chlorobenzenesulfonyl chloride.
Yield: 88%
NMR (CDCl$_3$): 1.7 (m, 14H), 2.7 (s, 2H), 2.8 (m, 4H), 3.6 (t, J=7.4 Hz, 2H), 3.9 (m, 1H), 4.2 (t, J=6.3 Hz, 1H), 6.9 (d, J=8.0 Hz, 2H), 7.1 (m, 2H), 7.5 (m, 2H), 7.7 (m, 2H)
LC-MS: ES+ 462.3 464.3 484.3 486.2 1 chlorine atom

1.4 EXAMPLES 7 TO 10

Obtained by working as in Example 6.

b) 4-[2-(Cyclopentylthio)ethyl]benzoic acid

Obtained by working as in Example 1b.
Yield: 59%
NMR (DMSO-d$_6$): 1.5 (m, 6H), 1.9 (m, 2H), 2.8 (m, 2H), 2.9 (m, 2H), 3.1 (m, 1H), 7.4 (d, J=8.2 Hz, 2H), 7.9 (d, J=8.2 Hz, 2H), 12.8 (s, 1H)

c) Methyl 4-[2-(cyclopentylthio)ethyl]benzoate

Obtained by working as in Example 6c.
Yield: 95%
NMR (DMSO-d$_6$): 1.5 (m, 6H), 1.9 (m, 2H), 2.7 (m, 2H), 2.9 (m, 2H), 3.0 (m, 1H), 3.8 (s, 3H), 7.2 (m, 2H), 7.9 (t, J=8.1 Hz, 2H)

d) {4-[2-(Cyclopentylthio))ethyl]phenyl}methanol

Obtained by working as in Example 6d.
Yield: quantitative
NMR (CDCl$_3$): 1.5 (m, 7H), 1.8 (m, 2H), 2.6 (m, 2H), 2.7 (m, 2H), 3.0 (m, 1H), 4.5 (s, 2H), 7.2 (m, 4H)

TABLE 2

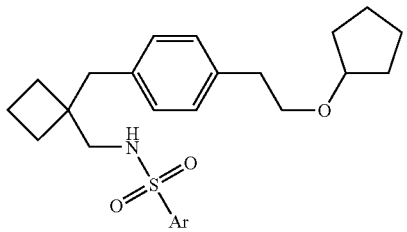

| Ex | Ar | NMR | LC-MS |
|---|---|---|---|
| 7 | 2,4-Dichlorophenyl | 1.7 (m, 14H), 2.7 (s, 2H), 2.8 (m, J = 7.2, 7.2 Hz, 4H), 3.6 (t, J = 7.3 Hz, 2H), 3.9 (dd, J = 5.4, 3.5 Hz, 1H), 4.8 (t, J = 6.4 Hz, 1H), 7.0 (d, J = 8.0 Hz, 2H), 7.1 (m, 2H), 7.4 (dd, J = 8.5, 2.0 Hz, 1H), 7.5 (d, J = 2.1 Hz, 1H), 8.0 (d, J = 8.4 Hz, 1H) | ES+ 496.2 498.2 500.2 518.2 520.2 522.2 2 chlorine atoms |
| 8 | 4-Methylphenyl | 1.7 (m, 14H), 2.4 (s, 3H), 2.7 (s, 2H), 2.8 (m, 4H), 3.6 (t, J = 7.4 Hz, 2H), 3.9 (m, 1H), 4.2 (t, J = 6.5 Hz, 1H), 7.0 (d, J = 8.2 Hz, 2H), 7.1 (m, 2H), 7.3 (m, 2H), 7.7 (d, J = 8.2 Hz, 2H) | ES+ 442.4 464.3 |
| 9 | 4-Methoxyphenyl | 1.7 (m, 14H), 2.7 (s, 2H), 2.8 (m, J = 14.2, 7.0 Hz, 4H), 3.6 (t, J = 7.4 Hz, 2H), 3.9 (m, 1H), 3.9 (s, 3H), 4.1 (t, J = 6.5 Hz, 1H), 7.0 (m, 4H), 7.1 (m, 2H), 7.8 (m, 2H) | ES+ 480.4 ES− 456.4 |
| 10 | 1-Naphthyl | 1.7 (m, 14H), 2.6 (s, 2H), 2.8 (m, 4H), 3.5 (t, J = 7.5 Hz, 2H), 3.9 (dd, J = 5.2, 3.7 Hz, 1H), 4.4 (t, J = 6.3 Hz, 1H), 6.8 (d, J = 7.8 Hz, 2H), 6.9 (d, J = 8.0 Hz, 2H), 7.5 (m, 1H), 7.7 (m, 2H), 8.0 (d, J = 8.0 Hz, 1H), 8.1 (d, J = 8.2 Hz, 1H), 8.2 (dd, J = 7.3, 1.0 Hz, 1H), 8.6 (d, J = 8.4 Hz, 1H) | ES+ 500.3 |

1.5 EXAMPLE 11

4-Chloro-N-[(1-{4-[2-(cyclopentylthio)ethyl]benzyl}cyclobutyl)methyl]benzenesulfonamide a) 1-Bromo-4-[2-(cyclopentylthio)ethyl]benzene Obtained by working as in Example 1a, starting with 2-(4-bromophenyl)ethyl methanesulfonate (Carbohydr. Res. (2003) 338, 29) and cyclopentanethiol.
Yield: 79%
NMR (CDCl$_3$): 1.5 (m, 4H), 1.7 (m, 2H), 2.0 (m, 2H), 2.8 (m, 4H), 3.1 (m, 1H), 7.1 (m, 2H), 7.4 (m, 2H)

e) 1-(Chloromethyl)-4-[2-(cyclopentylthio)ethyl]benzene

Obtained by working as in Example 1d.
Yield: 30%
NMR (CDCl$_3$): 1.5 (m, 4H), 1.7 (m, 2H), 1.9 (m, 2H), 2.7 (m, 2H), 2.8 (m, 2H), 3.1 (m, 1H), 4.5 (s, 2H), 7.1 (d, J=8.0 Hz, 2H), 7.3 (m, 2H)

f) 1-{4-[2-(Cyclopentylthio)ethyl]benzyl}cyclobutanecarbonitrile

Obtained by working as in Example 1e.
Yield: 55%

NMR (CDCl$_3$): 1.6 (m, 4H), 1.8 (m, 2H), 2.1 (m, 3H), 2.2 (m, 3H), 2.5 (m, 2H), 2.8 (m, 2H), 2.9 (m, 2H), 3.0 (s, 2H), 3.2 (m, 1H), 7.3 (m, 4H)

g) [(1-{4-[2-(Cyclopentylthio)ethyl]benzyl}cyclobutyl)methyl]amine

Obtained by working as in Example 1f.

Yield: 63%

NMR (CDCl$_3$): 1.7 (m, 4H), 2.0 (m, 12H), 2.8 (s, 2H), 3.0 (m, 6H), 3.2 (m, 1H), 7.2 (m, 4H)

h) 4-Chloro-N-[(1-{4-[2-(cyclopentylthio)ethyl]benzyl}cyclobutyl)methyl]-benzenesulfonamide Obtained by working as in Example 1g, starting with 4-chlorobenzenesulfonyl chloride.

Yield: 81%

NMR (CDCl$_3$): 1.7 (m, 14H), 2.7 (s, 2H), 2.8 (m, 6H), 3.1 (m, 1H), 4.2 (t, J=6.2 Hz, 1H), 7.0 (d, J=8.0 Hz, 2H), 7.1 (m, 2H), 7.5 (m, 2H), 7.7 (m, 2H)

LC-MS: ES− 476.4 478.4 1 chlorine atom

1.6 EXAMPLES 12 TO 20

Obtained by working as in Example 11.

TABLE 3

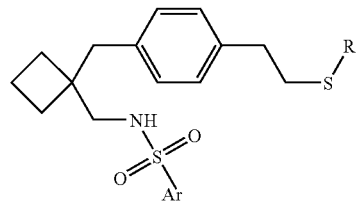

| Ex | R | Ar | NMR | LC-MS |
|---|---|---|---|---|
| 12 | Cyclopentyl | 2,4-Dichlorophenyl | 1.8 (m, 14H), 2.7 (s, 2H), 2.8 (m, 6H), 3.1 (m, 1H), 4.8 (t, J = 6.5 Hz, 1H), 7.1 (m, J = 8.1 Hz, 4H), 7.4 (dd, J = 8.5, 2.0 Hz, 1H), 7.5 (d, J = 2.0 Hz, 1H), 8.0 (d, J = 8.5 Hz, 1H) | ES+ 512.2 514.2 516.2 534.1 536.1 538.0 ES− 510.2 512.2 514.2 2 chlorine atoms |
| 13 | Cyclopentyl | 4-Methylphenyl | 1.8 (m, 14H), 2.4 (s, 3H), 2.7 (s, 2H), 2.8 (m, 6H), 3.1 (m, 1H), 4.2 (t, J = 6.5 Hz, 1H), 7.0 (d, J = 8.0 Hz, 2H), 7.1 (m, 2H), 7.3 (d, J = 8.0 Hz, 2H), 7.7 (d, J = 8.2 Hz, 2H) | ES+ 458.2 480.2 |
| 14 | Cyclopentyl | 4-Methoxyphenyl | 1.7 (m, 14H), 2.7 (s, 2H), 2.8 (m, 6H), 3.1 (m, 1H), 3.9 (s, 3H), 4.1 (t, J = 6.5 Hz, 1H), 7.0 (m, 4H), 7.1 (m, 2H), 7.7 (m, 2H) | ES+ 474.2 496.2 ES− 472.3 |
| 15 | Cyclopentyl | 1-Naphthyl | 1.7 (m, 12H), 2.0 (dd, J = 7.2, 5.0 Hz, 2H), 2.6 (s, 2H), 2.7 (m, 6H), 3.1 (m, 1H), 4.4 (t, J = 6.2 Hz, 1H), 6.8 (d, J = 8.0 Hz, 2H), 6.9 (d, J = 8.0 Hz, 2H), 7.5 (m, 1H), 7.7 (m, 2H), 8.0 (d, J = 7.8 Hz, 1H), 8.1 (d, J = 8.2 Hz, 1H), 8.2 (dd, J = 7.2, 1.1 Hz, 1H), 8.6 (d, J = 8.2 Hz, 1H) | ES+ 494.3 516.2 |
| 16 | Methyl | 4-Chlorophenyl | 1.8 (m, 6H), 2.1 (s, 3H), 2.7 (m, 4H), 2.8 (m, 4H), 4.2 (t, J = 6.2 Hz, 1H), 6.9 (m, 2H), 7.1 (m, 2H), 7.5 (m, 2H), 7.7 (m, 2H) | ES+ 424.1 426.1 1 chlorine atom |
| 17 | Methyl | 2,4-Dichlorophenyl | 1.8 (m, 6H), 2.1 (s, 3H), 2.8 (m, 8H), 4.8 (t, J = 6.3 Hz, 1H), 7.1 (m, 4H), 7.4 (m, 1H), 7.5 (t, J = 2.2 Hz, 1H), 8.0 (d, J = 8.4 Hz, 1H) | ES+ 458.1 460.1 462.2 ES− 456.2 458.2 460.2 2 chlorine atoms |
| 18 | Methyl | 4-Methylphenyl | 1.8 (m, 6H), 2.1 (s, 3H), 2.4 (s, 3H), 2.7 (m, 4H), 2.8 (m, 4H), 4.1 (m, 1H), 7.0 (m, 2H), 7.1 (m, 2H), 7.3 (d, J = 8.0 Hz, 2H), 7.7 (d, J = 8.2 Hz, 2H) | ES+ 404.2 426.2 |
| 19 | Methyl | 4-Methoxyphenyl | 1.8 (m, 6H), 2.1 (s, 3H), 2.7 (m, 4H), 2.8 (m, 4H), 3.9 (s, 3H), 4.1 (m, 1H), 7.0 (m, 4H), 7.1 (m, 2H), 7.7 (m, 2H) | ES+ 420.2 442.2 |
| 20 | Methyl | 1-Naphthyl | 1.7 (m, 6H), 2.1 (s, 3H), 2.6 (m, 4H), 2.8 (m, 4H), 4.4 (t, J = 6.3 Hz, 1H), 6.8 (m, 2H), 6.9 (m, 2H), 7.5 (m, 1H), 7.7 (m, 2H), 8.0 (m, 1H), 8.1 (d, J = 8.2 Hz, 1H), 8.2 (dd, J = 7.3, 1.2 Hz, 1H), 8.6 (d, J = 8.6 Hz, 1H) | ES+ 440.2 462.2 |

1.7 EXAMPLE 21

4-Chloro-N-[(1-{4-[2-(cyclopentylsulfonyl)ethyl]benzyl}cyclobutyl)methyl]benzenesulfonamide To a solution of 20 mg (0.042 mmol) of the compound prepared in Example 11, in 1 ml of dichloromethane, are added 28.125 mg (0.125 mmol) of meta-chloroperbenzoic acid.

After stirring for 16 hours at room temperature, the reaction medium is diluted with 10 ml of ethyl ether and washed twice with saturated NaHCO$_3$ solution and then with water, after which the organic phase is dried over Na$_2$SO$_4$. After concentrating under vacuum and purifying by flash chromatography on silica gel in a dichloromethane/ethyl acetate mixture (98/2), 21 mg of a light-beige solid are obtained.

Yield: 98%

NMR (CDCl$_3$): 1.9 (m, 14H), 2.7 (s, 2H), 2.9 (d, J=6.5 Hz, 2H), 3.2 (m, 5 H), 4.2 (t, J=6.4 Hz, 1H), 7.0 (d, J=8.0 Hz, 2H), 7.1 (m, 2H), 7.5 (m, 2 H), 7.8 (m, 2H)

LC-MS: ES+ 510.3 512.3 1 chlorine atom

1.8 EXAMPLES 22 TO 30

Obtained by working as in Example 21.

TABLE 4

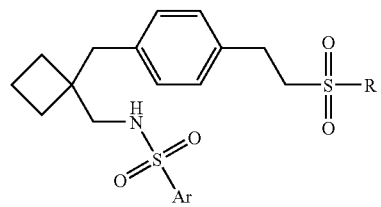

| Ex. | R | Ar | NMR | LC-MS |
|---|---|---|---|---|
| 22 | Cyclopentyl | 2,4-Dichlorophenyl | 1.7 (m, 4H), 1.9 (m, 10H), 2.7 (s, 2H), 2.8 (d, J = 6.5 Hz, 2H), 3.2 (m, 4H), 3.3 (m, 1H), 4.8 (t, J = 6.3 Hz, 1H), 7.1 (m, 4H), 7.4 (dd, J = 8.5 Hz, 2.0 Hz, 1H), 7.5 (d, J = 2.1 Hz, 1H), 8.0 (d, J = 8.4 Hz, 1H) | ES+ 544.1 546.1 548.1 566.1 568.1 517.1 2 chlorine atoms |
| 23 | Cyclopentyl | 4-Methylphenyl | 1.7 (m, 4H), 1.9 (m, 10H), 2.4 (s, 3H), 2.7 (s, 2H), 2.8 (d, J = 6.5 Hz, 2H), 3.1 (m, 4H), 3.3 (m, 1H), 4.1 (t, J = 6.5 Hz, 1H), 7.1 (m, 4H), 7.3 (m, 2H), 7.7 (m, 2H) | ES+ 490.3 512.3 ES− 488.4 |
| 24 | Cyclopentyl | 4-Methoxyphenyl | 1.7 (m, 4H), 1.9 (m, 10H), 2.7 (s, 2H), 2.8 (d, J = 6.5 Hz, 2H), 3.1 (m, 4H), 3.3 (m, 1H), 3.9 (s, 3H), 4.1 (t, J = 6.4 Hz, 1H), 7.0 (m, 6H), 7.8 (m, 2H) | ES+ 506.3 528.3 ES− 504.4 |
| 25 | Cyclopentyl | 1-Naphthyl | 1.7 (m, 14H), 2.6 (s, 2H), 2.8 (d, J = 6.3 Hz, 2H), 3.1 (m, 4H), 3.3 (m, 1H), 4.4 (t, J = 6.1 Hz, 1H), 6.8 (d, J = 8.0 Hz, 2H), 6.9 (m, 2H), 7.5 (m, 1H), 7.7 (m, 2H), 8.0 (d, J = 7.6 Hz, 1H), 8.1 (d, J = 8.2 Hz, 1H), 8.2 (dd, J = 7.2, 1.1 Hz, 1H), 8.6 (d, J = 8.2 Hz, 1H) | ES+ 526.3 548.3 ES+ 524.4 |
| 26 | Methyl | 4-Chloropentyl | 1.7 (m, 2H), 1.9 (m, 4H), 2.7 (s, 2H), 2.8 (s, 3H), 2.9 (d, J = 6.5 Hz, 2H), 3.1 (m, 2H), 3.3 (m, 2H), 4.2 (t, J = 6.2 Hz, 1H), 7.0 (d, J = 8.0 Hz, 2H), 7.1 (m, 2H), 7.5 (m, 2H), 7.8 (m, 2H) | ES− 454.3 456.3 |
| 27 | Methyl | 2,4-Dichlorophenyl | 1.7 (m, 2H), 1.9 (m, 4H), 2.8 (s, 2H), 2.8 (d, J = 6.5 Hz, 2H), 2.8 (s, 3H), 3.1 (m, 2H), 3.3 (m, 2H), 4.8 (t, J = 6.3 Hz, 1H), 7.1 (m, 4H), 7.4 (dd, J = 8.5, 2.0 Hz, 1H), 7.5 (d, J = 2.0 Hz, 1H), 8.0 (d, J = 8.5 Hz, 1H) | ES− 488.3 490.3 492.3 2 chlorine atoms |
| 28 | Methyl | 4-Methylphenyl | 1.7 (m, 2H), 1.8 (m, 4H), 2.4 (s, 3H), 2.7 (s, 2H), 2.8 (s, 3H), 2.8 (d, J = 6.4 Hz, 2H), 3.1 (m, 2H), 3.3 (m, 2H), 4.2 (t, J = 6.4 Hz, 1H), 7.1 (m, 4H), 7.3 (d, J = 8.4 Hz, 2H), 7.7 (d, J = 8.4 Hz, 2H) | ES+ 436.3 458.3 ES− 434.4 |
| 29 | Methyl | 4-Methoxyphenyl | 1.7 (m, 2H), 1.8 (m, 4H), 2.7 (s, 2H), 2.8 (m, 5H), 3.1 (m, 2H), 3.3 (m, 2H), 3.9 (s, 3H), 4.1 (t, J = 6.4 Hz, 1H), 7.0 (m, 2H), 7.1 (m, 4H), 7.7 (m, 2H) | ES+ 452.2 474.1 ES− 450.2 |
| 30 | Methyl | 1-Naphthyl | 1.6 (m, 2H), 1.8 (m, 4H), 2.6 (s, 2H), 2.8 (d, J = 6.3 Hz, 2H), 2.8 (s, 3H), 3.1 (m, 2H), 3.2 (m, 2H), 4.4 (t, J = 6.3 Hz, 1H), 6.8 (d, J = 8.0 Hz, 2H), 6.9 (m, 2H), 7.5 (t, J = 7.4 Hz, 1H), 7.7 (m, 2H), 8.0 (d, J = 8.2 Hz, 1H), 8.1 (d, J = 8.2 Hz, 1H), 8.2 (d, J = 7.4 Hz, 1H), 8.6 (d, J = 8.6 Hz, 1H) | ES− 470.4 |

1.9 EXAMPLE 31

N-({1-[4-(2-tert-Butoxyethyl)benzyl]cyclopentyl}methyl)-4-methylbenzenesulfonamide To a solution of 50 mg (0.129 mmol) of N-({1-[4-(2-hydroxyethyl)benzyl-cyclopentyl}methyl)-4-methylbenzenesulfonamide (EP 472 449) in 0.4 ml of THF are added at room temperature 25.4 µl (0.138 mmol) of tert-butyl 2,2,2-trichloro-ethanimidoate, followed by 3 µl of boron trifluoride etherate. After stirring for 16 hours at room temperature, 10 ml of ethyl ether are added to the reaction medium, followed by washing with saturated NaHCO$_3$ solution and then with water, and drying of the organic phase over Na$_2$SO$_4$. After concentrating under vacuum and purifying the residue by flash chromatography on silica gel with a dichloromethane/ethyl acetate mixture (9/1), 8.2 mg of oil are obtained.

Yield: 14%

NMR (CDCl$_3$): 1.3 (m, 2H), 1.5 (m, 15H), 2.4 (s, 3H), 2.6 (s, 2H), 2.7 (d, J=6.3 Hz, 2H), 2.8 (t, J=6.4 Hz, 2H), 3.8 (t, J=6.4 Hz, 2H), 4.1 (t, J=6.3 Hz, 1H), 7.0 (m, 4H), 7.3 (d, J=8.0 Hz, 2H), 7.7 (d, J=8.0 Hz, 2H)

LC-MS: ES+ 466.3

1.10 EXAMPLE 32

4-Chloro-N-[(1-{4-[2-(pyrid-2-yloxy)ethyl]benzyl}cyclopentyl)methyl]benzenesulfonamide A mixture of 30 mg (0.074 mmol) of 4-chloro-N-({1-[4-(2-hydroxyethyl)benzyl]cyclopentyl}methyl]benzenesulfonamide (EP 472449), 130 µl (1.48 mmol) of 2-fluoropyridine and 16.576 mg (0.148 mmol) of potassium carbonate is irradiated in a microwave oven (600 W max.), at a maximum temperature of 120° C. for 4 minutes. The crude reaction medium is purified by preparative LC-MS to give 8 mg of the expected compound.

Yield: 22.3%

LC-MS: ES+ 485.5 487.5 1 chlorine atom

1.11 EXAMPLES 33 TO 50

These examples were obtained as described in patent EP 472 449.

1.12 EXAMPLE 51

N-({1-[4-(2-Hydroxyethyl)benzyl]cyclopentyl}methyl)naphthalene-2-sulfonamide 2 g of Dowex 50 W X8-400 resin washed successively in a chromatography column with 50 ml of 6N HCl, 100 ml of water and then 50 ml of methanol.

This washed resin is added to a solution of 114 mg (0.225 mmol) of N-[(1-{4-[2-tetrahydro-2H-pyran-2-yloxy)ethyl]benzyl}cyclopentyl}methyl)naphthalene-2-sulfonamide (EP 472 449) in 5 ml of methanol.

After stirring for 2 hours at room temperature, the resin is filtered off and is then rinsed with methanol. The combined filtrates are concentrated to give 90 mg of the expected compound.

Yield: 94.6%

NMR (CDCl$_3$): 1.4 (m, 8H), 2.6 (s, 2H), 2.8 (m, 4H), 3.5 (s, 1H), 3.8 (t, J=6.4 Hz, 2H), 4.2 (t, J=6.6 Hz, 1H), 6.9 (m, 4H), 7.6 (m, 2H), 7.8 (dd, J=8.7, 1.8 Hz, 1H), 8.0 (m, 3H), 8.4 (d, J=1.5 Hz, 1H)

LC-MS: ES+ 424.3 ES− 422.3

1.13 EXAMPLES 52 AND 53

Obtained by working as in Example 51.

TABLE 5

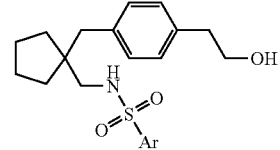

| Ex | Ar | NMR | LC-MS |
|---|---|---|---|
| 52 | 4-nitrophenyl | 1.5 (m, 8H), 2.6 (s, 2H), 2.8 (d, J = 6.3 Hz, 2H), 2.8 (m, 2H), 3.5 (s, 1H), 3.8 (t, J = 6.4 Hz, 2H), 4.3 (t, J = 6.3 Hz, 1H), 7.1 (m, 4H), 8.0 (m, 2H), 8.3 (m, 2H) | ES+ 419.3 ES− 417.3 |
| 53 | 4-cyclohexylphenyl | | ES+ 456.3 ES− 454.3 |

1.14 EXAMPLE 54

N-({1-[4-(2-Hydroxyethyl)benzyl]cyclopentyl}methyl)pyridine-3-sulfonamide

To a mixture of 300 mg (1.086 mmol) of 2-(4-{[1-(aminomethyl)-cyclo-pentyl]methyl}phenyl)ethanol (EP 472 449), 30 ml of dichloromethane and 537.6 µl (3.857 mmol) of triethylamine is added dropwise, at −20° C., a solution of 310.1 mg (1.222 mmol) of 3-pyridinesulfonyl chloride in 10 ml of dichloromethane. The mixture is allowed to warm to room temperature slowly (over 3 hours) and is stirred for a further 2 hours. The reaction medium is then washed with water and dried over Na$_2$SO$_4$. After concentrating the organic phase under vacuum, the oil obtained is purified by flash chromatography on silica gel with a dichloromethane/methanol mixture (99/1). 266 mg of an amorphous white solid are obtained.

Yield: 55.3%

NMR (DMSO-d$_6$): 1.4 (m, 8H), 2.6 (m, 6H), 3.5 (m, 2H), 4.6 (t, J=5.1 Hz, 1H), 7.0 (m, 4H), 7.6 (m, 1H), 7.8 (s, 1H), 8.2 (dd, J=8.0, 1.3 Hz, 1 H), 8.8 (m, 1H), 8.9 (d, J=1.3 Hz, 1H)

LC-MS: ES+ 375.3 ES− 373.3

1.15 EXAMPLE 55

4-Chloro-N-({1-[4-(2-hydroxyethyl)benzyl]cyclopropyl}methyl)benzenesulfonamide To a solution of 200 mg (0.508 mmol) of (4-{[1-({[(4-chlorophenyl)sulfonyl]amino}methyl)cyclopropyl]methyl}phenyl)acetic acid (EP 472 449) in 10 ml of THF are added, at 15° C., 280 µl (0.559 mmol) of a 2M solution of BH$_3$-Me$_2$S in toluene. After warming to room temperature, the reaction medium is stirred for 2 hours.

While maintaining the reaction medium at 20° C., 6 ml of water and 6 ml of toluene are added, followed by addition of 77.2 mg (0.559 mmol) of K$_2$CO$_3$ dissolved in 6 ml of water, and then of a further 6 ml of toluene.

After separation of the phases by settling, the organic phase is washed with water and then dried over Na$_2$SO$_4$ and concentrated under vacuum to give 236 mg of a pure white solid.

Yield: quantitative

NMR (CDCl$_3$): 0.4 (m, 2H), 0.5 (m, 2H), 2.6 (s, 2H), 2.7 (d, J=6.0 Hz, 2H), 2.8 (t, J=6.5 Hz, 2H), 3.9 (t, J=6.5 Hz, 2H), 4.2 (m, 1H), 7.0 (d, J=7.9 Hz, 2H), 7.1 (m, 2H), 7.4 (m, 2H), 7.7 (m, 2H)

LC-MS: ES− 378.2 380.2 1 chlorine atom

1.16 EXAMPLES 56 AND 57

Obtained by working as in Example 55.

TABLE 6

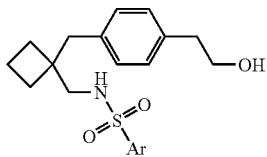

| Ex | Ar | NMR | LC-MS |
|---|---|---|---|
| 56 | 4-chlorophenyl | 1.8 (m, 6H), 2.7 (s, 2H), 2.8 (m, 4H), 3.8 (t, J = 6.4 Hz, 2H), 4.1 (s, 1H), 7.0 (d, J = 7.9 Hz, 2H), 7.1 (m, 2H), 7.5 (d, J = 8.7 Hz, 2H), 7.7 (d, J = 8.7 Hz, 2H) | ES− 392.2 394.2 1 chlorine atom |
| 57 | 4-methylphenyl | 1.8 (m, 6H), 2.4 (m, 3H), 2.7 (m, 2H), 2.8 (m, 4H), 3.8 (m, 2H), 4.1 (m, 1H), 7.0 (m, 2H), 7.1 (m, 2H), 7.3 (m, 2H), 7.7 (m, 2H) | ES+ 374.3 396.2 ES− 372.3 |

1.17 EXAMPLE 58

2,3,4,5,6-Pentafluoro-N-({1-[4-(2-hydroxyethyl)benzyl]cyclopentyl}methyl)benzenesulfonamide Obtained by working as in Example 51.

Yield: 89.8%

NMR (CDCl$_3$): 1.5 (m, 8H), 2.7 (s, 2H), 2.8 (t, J=6.5 Hz, 2H), 2.9 (d, J=6.7 Hz, 2H), 3.8 (t, J=6.5 Hz, 2H), 4.7 (m, 1H), 7.1 (m, 4H)

LC-MS: ES+ 446 464 486

1.18 EXAMPLES 59 AND 60

Obtained by working as in Example 55.

TABLE 7

| Ex | Ar | NMR | LC-MS |
|---|---|---|---|
| 59 | 4-methylphenyl | 1.5 (m, 8H), 2.4 (s, 3H), 2.6 (s, 2H), 2.7 (d, J = 6.5 Hz, 2H), 2.8 (t, J = 6.5 Hz, 2H), 3.8 (s, 2H), 4.2 (t, J = 6.5 Hz, 1H), 7.0 (d, J = 8.0 Hz, 2H), 7.1 (m, 2H), 7.3 (d, J = 8.4 Hz, 2H), 7.7 (d, J = 8.4 Hz, 2H) | ES+ 388.3 410.3 ES− 386.3 |
| 60 | phenyl | 1.4 (m, 8H), 2.6 (s, 2H), 2.7 (d, J = 6.5 Hz, 2H), 2.8 (t, J = 6.4 Hz, 2H), 3.8 (t, J = 6.4 Hz, 2H), 4.2 (t, J = 6.5 Hz, 1H), 5.3 (s, 1H), 7.0 (m, 2H), 7.1 (m, 2H), 7.5 (m, 3H), 7.8 (m, 2H) | ES+ 374.3 396.3 ES− 372.3 |

1.19 EXAMPLES 61 TO 63

Obtained by working as in Example 54.

TABLE 8

| Ex | Ar | NMR | LC-MS |
|---|---|---|---|
| 61 | 3,4,5-trifluorophenyl | 1.5 (m, 8H), 2.6 (m, 2H), 2.7 (m, 2H), 2.8 (m, 2H), 3.9 (q, J = 6.2 Hz, 2H), 4.1 (t, J = 6.4 Hz, 1H), 7.0 (m, 2H), 7.1 (m, 2H), 7.4 (m, 2H) | ES− 426.4 |
| 62 | 3,5-dichlorophenyl | 1.5 (m, 8H), 2.6 (m, 2H), 2.7 (d, J = 6.3 Hz, 2H), 2.8 (t, J = 6.4 Hz, 2H), 3.8 (m, 2H), 4.1 (t, J = 6.2 Hz, 1H), 7.0 (m, 2H), 7.1 (m, 2H), 7.5 (m, 1H), 7.6 (m, 2H) | ES− 440.4 442.4 444.4 2 chlorine atoms |
| 63 | 3-methylphenyl | 1.5 (m, 8H), 2.4 (s, 3H), 2.6 (m, 2H), 2.7 (m, 2H), 2.8 (t, J = 6.5 Hz, 2H), 3.8 (m, J = 6.4, 6.4 Hz, 2H), 4.1 (t, J = 6.5 Hz, 1H), 5.3 (s, 1H), 7.0 (m, 2H), 7.1 (m, 2H), 7.4 (m, 2H), 7.6 (m, 2H) | ES+ 388.4 410.4 ES− 386.5 |

1.20 EXAMPLE 64

4-Fluoro-N-({1-[4-(2-hydroxyethyl)benzyl]cyclopentyl}methyl)benzenesulfonamide Obtained by working as in Example 55.
Yield: 97.4
NMR (CDCl$_3$): 1.4 (m, 8H), 2.6 (s, 2H), 2.7 (d, J=6.5 Hz, 2H), 2.8 (t, J=6.5 Hz, 2H), 3.5 (s, 1H), 3.8 (t, J=6.5 Hz, 2H), 4.1 (t, J=6.5 Hz, 1H), 7.0 (m, 2H), 7.1 (m, 2H), 7.2 (m 2H), 7.8 (m, 2H)
LC-MS: ES+ 392.4 414.4 ES− 390.4

1.21 EXAMPLE 65

4-Chloro-N-({1-[4-(2-hydroxyethyl)benzyl]cyclopentyl}methyl)-3-(trifluoromethyl)-benzenesulfonamide Obtained by working as in Example 54.
Yield: 55.9%
NMR (CDCl$_3$): 1.4 (m, 8H), 2.6 (m, 2H), 2.7 (m, 2H), 2.8 (t, J=6.4 Hz, 2 H), 3.8 (m, 2H), 4.2 (t, J=5.7 Hz, 1H), 5.3 (m, 1H), 7.0 (m, 2H), 7.1 (m, 2H), 7.7 (m, 1H), 7.9 (m, 1H), 8.1 (s, 1H)

1.22 EXAMPLE 66

2,3,4,5,6-Pentafluoro-N-[{1-[4-(2-hydroxyethyl)benzyl]cyclobutyl}methyl]benzene-sulfonamide a) 1-[4-(2-Hydroxyethyl)benzyl]cyclobutanecarbonitrile

To a solution, under a nitrogen atmosphere, of 12.649 ml (90 mmol) of diisopropylamine in 180 ml of THF, maintained at −20° C., are added 56.25 ml (90 mmol) of a 1.6M solution of n-butyllithium in hexane. After stirring for 15 minutes, a solution of 6.652 g (82 mmol) of cyclobutanecarbonitrile in 20 ml of THF is added. After stirring for 30 minutes at −20° C., a solution of 24.6 g (82 mmol) of 2-[2-(4-ethylphenyl)ethoxy]tetrahydro-2H-pyran in 60 ml of THF is added. The reaction medium is stirred at −20° C. for one hour and then at room temperature for 24 hours.

3.2 ml of water and 160 ml of toluene are then added, the mixture is stirred vigorously for 30 minutes and the organic phase is then washed successively with saturated NaCl solution, with 10% HCl solution (twice) and then again with saturated aqueous NaCl solution. The organic phase, dried over Na$_2$SO$_4$, is concentrated under vacuum to give 24.1 g of oil, which is used without further purification.

A Dowex 50W X8-400 resin (65 g) is successively washed with 6N HCl (500 ml), H$_2$O (500 ml) and then methanol (500 ml). After filtration, a solution composed of 24.1 g of oil obtained above and 200 ml of methanol is added. The mixture is stirred for 6 hours at room temperature and left to stand for 16 hours.

After filtering and concentrating the methanol, 15.6 g of a brown oil are obtained.
Yield: 88%
NMR (CDCl$_3$): 2.3 (m, 5H), 2.6 (m, 2H), 3.0 (t, J=6.6 Hz, 2H), 3.1 (s, 2 H), 4.0 (t, J=6.6 Hz, 2H), 7.4 (m, 4H)
LC-MS: (ES+) 431.3 (2M+H)

b) 2-(4-{[1-(Aminomethyl)cyclobutyl]methyl}phenyl)ethanol

Obtained by working as in Example 1f, starting with the compound prepared in Example 66a.
Yield: quantitative
NMR (CDCl$_3$): 1.6 (m, 7H), 2.4 (s, 2H), 2.7 (m, 4H), 3.6 (m, 4H), 7.0 (m, 4H)
LC-MS: (ES+) 220.2 c) 2,3,4,5,6-Pentafluoro-N-({1-[4-(2-hydroxyethyl)benzyl]cyclobutyl}-methyl)benzenesulfonamide Obtained by working as in Example 54, starting with the compound prepared in Example 66b and 2,3,4,5,6-pentafluorobenzenesulfonyl chloride.
Yield: 22.0%
NMR (CDCl$_3$): 1.9 (m, 6H), 2.8 (s, 2H), 3.0 (m, 4H), 3.7 (m, 2H), 4.8 (t, J=6.1 Hz, 1H), 7.1 (m, 4H)
LC-MS: ES− 466.3 468.3 1 chlorine atom

1.23 EXAMPLE 67

N-({1-[4-(2-(Hydroxyethyl]benzyl]cyclobutyl}methyl]-4-nitro-3-(trifluoromethyl)benzenesulfonamide a) [4-({1-[({[4-Nitro-3-(trifluoromethyl)phenyl]sulfonyl}amino)methyl]-cyclopentyl}methyl)phenyl]acetic acid To a solution composed of 335.436 mg (2.427 mmol) of potassium carbonate, 200 mg (0.809 mmol) of (4-{[1-(aminomethyl)cyclopentyl]methyl}acetic acid (EP 472 449) and 35 ml of water are added 257.471 mg (0.889 mmol) of 4-nitro-3-(trifluoromethyl)phenylsulfonyl chloride. The reaction mixture is maintained at 80° C. for 2.5 hours. After cooling, it is washed with ethyl ether. The aqueous phase is brought to pH 1 with HCl solution and extracted with dichloromethane. The organic phase is washed with H$_2$O and dried over Na$_2$SO$_4$ to give 177.6 mg of the expected compound.
Yield: 43.9%
NMR (CDCl$_3$): 1.6 (m, 8H), 2.6 (s, 2H), 2.8 (d, J=6.3 Hz, 2H), 3.6 (s, 2 H), 4.6 (t, J=6.3 Hz, 1H), 7.0 (d, J=8.0 Hz, 2H), 7.1 (m, 2H), 7.9 (d, J=8.4 Hz, 1H), 8.1 (m, 1H), 8.2 (d, J=1.7 Hz, 1H)

b) N-({1-[4-(2-Hydroxyethyl)benzyl]cyclopentyl}methyl)-4-nitro-3-(trifluoro-methyl)benzenesulfonamide Obtained by working as in Example 55.
Yield: 62%
NMR (CDCl$_3$): 1.5 (d, J=41.2 Hz, 8H), 2.6 (s, 2H), 2.8 (m, 4H), 3.9 (t, J=6.5 Hz, 2H), 4.2 (t, J=6.2 Hz, 1H), 7.0 (m, J=8.0 Hz, 2H), 7.1 (m, 2 H), 8.0 (m, J=8.4 Hz, 1H), 8.1 (m, 1H), 8.2 (s, 1H)
LC-MS: ES− 485.4

1.24 EXAMPLE 68

N-(Cyclopropylmethyl)-N-({1-[4-(2-(hydroxyethyl)benzyl]cyclobutyl}methyl]-4-methylbenzenesulfonamide A mixture of 30 mg (0.08 mmol) of the compound prepared in Example 57, 311.5 µl (3.212 mmol) of (bromomethyl)cyclopropane and 27.03 mg (0.241 mmol) of potassium carbonate is irradiated in a 600 W microwave oven at 110° C. for 8 minutes.

The reaction medium, taken up in ethyl acetate, is washed with water and dried over Na$_2$SO$_4$, and then concentrated under vacuum.

The residue obtained is purified by flash chromatography on silica gel with a dichloromethane/ethyl acetate mixture (9/1) to give 20.6 mg of solid.
Yield: 60%
NMR (DMSO-d$_6$): 0.0 (m, 2H), 0.3 (m, 2H), 0.7 (m, 1H), 1.4 (m, 2H), 1.8 (m, 2H), 2.0 (m, 2H), 2.4 (s, 3H), 2.7 (m, 4H), 3.0 (d, J=6.5 Hz, 2H), 3.2 (s, 2H), 3.6 (m, 2H), 4.6 (m, 1H), 7.1 (m, 4H), 7.4 (m, 2H), 7.7 (m, 2H)
LC-MS: ES+ 428.4 450.4

1.25 EXAMPLE 69

4-Chloro-N-(cyclopropylmethyl)-N-({1-[4-(2-(hydroxyethyl]benzyl]cyclobutyl}-methyl)benzenesulfonamide Obtained by working as in Example 68, starting with the compound prepared in Example 56.
Yield: 16.7%
LC-MS: ES+ 448.4 450.4 470.4 472.4 (1 chlorine atom)
Biochemical Test
2. Objective
Demonstration of inhibition of the activity of the chosen caspase by a delayed-time fluorescence method.
3. Principle of the Method
Caspases are cysteine proteases that have a strict specificity of cleavage of their substrate after an aspartic acid residue.
The substrate used is a tetrapeptide specific to this caspase, having at one of its ends a fluorescent europium marker (W1284) and at the other end a europium chelate fluorescence quencher (QSy-7): Eu-W1284-CIETDK-QSy-7. The europium chelate (W1284) and the fluorescence quencher (QSy-7) are protected molecules and the property of Wallac Oy, a division of Perkin Elmer.
The caspase cleaves the substrate, releasing the quencher. Thus, by excitation at 340 nm, the signal emitted by the fluorescence of the europium is read by WALLAC Victor$^2$ reader at 615 nm.
A product capable of inhibiting the activity of this enzyme will be detected by inhibition of the fluorescence relative to the fluorescence detected in the sample incubated without inhibitors (100%).
4. Procedure
Reagents
The caspase reaction buffer: the Pipes (piperazine-N,N'-bis[2-ethanesulfonic acid]), sucrose, EDTA-Na2 (disodium salt of ethylenediaminetetraacetic acid), CHAPS (3-[(3-cholamidopropyl)dimethylammonio]-1-propanesulfonate) and DTT (dithiothreitol) are obtained from Sigma, the sodium hydroxide (NaOH) as a 1N solution, NaCl and DMSO are of analytical grade and are obtained from Merck, and the distilled water is obtained from BDH Laboratories.
The caspase substrates: the substrate for caspases 2 and 3 is Eu-W1284-CDEVDK-QSy-7, the substrate for caspase-6 is Eu-W1284-CVEIDK-QSy-7, the substrate for caspases 8 and 10 is Eu-WI284-CIETDK-QSy-7 and the substrate for caspase-9 is Eu-W1284-CLEHDK-QSy-7, and they are all obtained from Wallac Oy, a division de Perkin Elmer.
Recombinant human caspases: caspases 2, 3, 6 and 10 are obtained from Biomol, except for caspase-8 and caspase-9, which are obtained from Calbiochem, a division of Merck Biosciences.
The standard caspase inhibitors: The irreversible inhibitor chosen as standard for caspase-2 is z-(benzyloxycarbonyl)-D(OMe)VAD(OMe)-fmk (fluoromethyl ketone), z-D(OMe) E(OMe)VD(OMe)-fmk for caspase-3, z-VE(OMe)ID (OMe)-fmk for caspase-6, z-IE(OMe)TD(OMe)-fmk for caspase-8 and caspase-10 and z-LE(OMe)HD(OMe)-fmk for caspase-9. All the inhibitors are obtained from Calbiochem, a division of Merck Biosciences.
The specific caspase-10 inhibitors are obtained from chemical synthesis on the base of the formula 1 and are supplied in powder form.
Preparation
The caspase buffer (H. R. Stennicke et al., J. Biol. Chem. 272 (1997) 25719-25723): 20 mM Pipes, 100 mM NaCl, 10 mM DTT, 0.1% CHAPS, 10% sucrose, 1 mM EDTA, pH 7.2.

The buffer is prepared in 9/10 of the final volume and stored at 4° C., followed by addition of 1/10 of the volume of DTT (100 mM) extemporaneously on the day of the assay.

The substrates: Stored at −80° C. and thawed on ice for 5-10 min. After pelletising the powder, the flask is opened and the contents are taken up in 0.4 ml of distilled $H_2O$ to obtain a final concentration of 10 μM. Dissolution is continued for 15 minutes on ice, and the substrate is then ready for use or may be divided into aliquots and stored at −80° C. The substrate is diluted 25× in the caspase buffer (400 nM) and then deposited (10 μl) in the assay well at a final concentration of 120 nM (dilution 1/3.3).

The caspases: All the caspases, except for caspase-9, which is freeze-dried, are supplied in solution form (50 U/μl). They are ready for use or may be divided into aliquots and stored at −80° C. The assay is performed with 25 U of caspase per well, the volume of enzyme (50 U/μl) adapted to the number of wells is taken up and diluted 40× in the caspase buffer (1.25 U/μl). 20 μl of this solution are distributed per well of the assay plate. For caspase-9, the lyophilisate is reconstituted in PBS (1 U/μl) and diluted 20× in the caspase buffer (0.05 U/μl). The assay is performed with 1 U of enzyme per well, by distributing 20 μl of the diluted solution per well.

The standard inhibitors: The standard inhibitors are dissolved in DMSO to a concentration of 10 mM. They are tested at $IC_{20}$ and at $IC_{50}$ on the caspases they inhibit (see following table). The concentrations mentioned in the table are the final concentrations in the assay wells.

|  | $IC_{50}$ | $IC_{20}$ |
|---|---|---|
| z-DVAD-fmk | 450 nM | 3 μM |
| z-DEVD-fmk | 600 nM | 1.5 μM |
| z-VEID-fmk | 1 μM | 3 μM |
| z-LEHD-fmk | 40 nM | 200 nM |
| z-IETD-fmk (caspase-8) | 800 nM | 1.5 μM |
| z-IETD-fmk (caspase-10) | 15 nM | 80 nM |

The standards for $IC_{20}$ and $IC_{50}$ are diluted to intermediate concentrations in DMSO (for example: 23.5 μM for z-IETD-fmk at 80 nM for caspase-10 and 4.41 μM for 15 nM) and all prediluted (1/26.67) in the caspase buffer (1.5 μl in 40 μl (final volume) of caspase buffer). They are then distributed in the wells using this solution to reach the final concentration of $IC_{20}$ or $IC_{50}$, i.e. 3 μl in 33 μl of final reaction volume (dilution 1/11). Thus, the final concentration of DMSO in the well is 0.3% (v/v) final. The factor z as described in Zhang et al. J. Biomol. Screen. 4 (1999) 67-73 is always greater than 0.5 for all the standard inhibitors listed in the above table, tested at $IC_{50}$ and compared with the respective control without inhibition (100%).

The specific caspase-10 inhibitors: The synthetic products are dissolved in DMSO to a concentration of 20 mM. An intermediate dilution (1/6.6) is prepared in DMSO by diluting 10 μl of the concentrated solution in 66 μl of DMSO (final volume). They are then prediluted (1/26.67) in the caspase buffer, as for the standards, by diluting 1.5 μl of this solution in 40 μl of buffer (final volume). The inhibitors are then distributed in the wells to reach the final screening concentration (10 μM), i.e. 3 μl in 33 μl of final reaction volume (dilution 1/11) and a final concentration of DMSO of 0.3% (v/v) in the well.
Protocol:
The assay is performed in black 384- or 96-well microassay plates (CO-STAR) with an untreated surface. The volumes and the protocol were optimised for automated use.

| TEST (total volume = 33 μl) | BLANK (total volume = 33 μl) |
|---|---|
| 20 μl buffer with enzyme<br>3 μl inhibitor or standard/<br>DMSO prediluted<br>10 μl substrate | 20 μl buffer<br>3 μl DMSO prediluted<br><br>10 μl substrate |

The incubation takes place for 3 hours 30 minutes at room temperature before reading the fluorescence in delayed time on the WALLAC Victor[2] reader with the filters corresponding to the fluorescence of europium (excitation filter: 340 nm, emission filter: 615 nm).

The inhibitors which have a signal ≦60% of the control without inhibitor (100%) and which are specific for caspase-10, i.e. which do not inhibit (≧60% of the control) the other caspases, are selected for the determination of the $IC_{50}$ on caspase-10 and the other caspases.

Determination of the $IC_{50}$ on caspase-10 and the other caspases: specificity of inhibition: Same protocol as described previously, the inhibitors selected for their specificity of inhibition of caspase-10 at 10 μm are then tested from 100 nM to 200 μM on caspase-10 and also on the other caspases (2, 3, 6, 8 and 9). The inhibitors are diluted using solutions with concentrations of less than 20 mM in DMSO, and then prediluted in the caspase buffer. These predilutions are prepared by diluting 5 μl of the stock solution in 40 μl of caspase buffer (final volume) and the various points of the concentration range (0.123; 0.37; 1.11, 3.3; 10; 25; 50; 75; 100 and 200 μM) are reached in the well by distributing 3 μl of these solutions in 33 μl of final volume (dilution 1/11). Similarly, the standard caspase-10 inhibitor at $IC_{50}$ and at $IC_{20}$ are prediluted by diluting 5 μl of the stock solution (7.9 μM in DMSO for $IC_{50}$, 80 nM) in 40 μl of caspase buffer. For the $IC_{50}$ values, the final DMSO concentration in the wells is 1% instead of 0.3% in the screening protocol. For the specific caspase-10 inhibitors, the $IC_{50}$ values are thus determined on all the caspases. The specificity factor for caspase-10 is calculated as the following ratio:

Specificity factor=ratio[$IC_{50}$caspase$x$/$IC_{50}$caspase-10]

with x=2, 3, 6, 8 or 9

The results are summarised in the following table:

| | Inhibition $IC_{50}$ (nM) | | | | | |
|---|---|---|---|---|---|---|
| Ex | Caspase-2 | Caspase-3 | Caspase-6 | Caspase-8 | Caspase-9 | Caspase-10 |
| 1 | >200000 | >200000 | >200000 | >200000 | >200000 | 220 |
| 5 | >200000 | >200000 | >200000 | >200000 | >200000 | 3588 |
| 12 | >200000 | >200000 | >200000 | >200000 | >200000 | 216 |
| 17 | >200000 | >200000 | >200000 | >200000 | >200000 | 214 |
| 22 | >200000 | >200000 | >200000 | >200000 | >200000 | 705 |
| 27 | >200000 | >200000 | >200000 | >200000 | >200000 | 235 |
| 30 | >200000 | >200000 | >200000 | >200000 | >200000 | 4460 |
| 33 | >200000 | >200000 | >200000 | >200000 | >200000 | 1701 |
| 34 | >200000 | >200000 | >200000 | >200000 | >200000 | 3495 |
| 35 | >200000 | >200000 | >200000 | >200000 | >200000 | 2881 |
| 36 | >200000 | >200000 | >200000 | >200000 | >200000 | 9662 |
| 43 | >200000 | >200000 | >200000 | >200000 | >200000 | 5123 |
| 45 | >200000 | >200000 | >200000 | >200000 | >200000 | 297 |
| 46 | >200000 | >200000 | >200000 | >200000 | >200000 | 179 |
| 47 | >200000 | >200000 | >200000 | >200000 | >200000 | 5506 |
| 49 | >200000 | >200000 | >200000 | >200000 | >200000 | 3142 |
| 50 | >200000 | >200000 | >200000 | >200000 | >200000 | 3160 |
| 51 | >200000 | >200000 | >200000 | >200000 | >200000 | 281 |
| 52 | >200000 | >200000 | >200000 | >200000 | >200000 | 3694 |
| 56 | >200000 | >200000 | >200000 | >200000 | >200000 | 989 |
| 57 | >200000 | >200000 | >200000 | >200000 | >200000 | 3051 |
| 58 | >200000 | >200000 | >200000 | >200000 | 46719 | 143 |
| 59 | >200000 | >200000 | >200000 | >200000 | >200000 | 4061 |
| 61 | >200000 | >200000 | >200000 | >200000 | >200000 | 1788 |
| 62 | >200000 | >200000 | >200000 | >200000 | >200000 | 6215 |
| 63 | >200000 | >200000 | >200000 | >200000 | >200000 | 6563 |
| 65 | >200000 | >200000 | >200000 | >200000 | >25000 | 250 |
| 66 | >200000 | >200000 | >200000 | >200000 | >200000 | 393 |

The invention claimed is:

1. A method for treating retinopathy comprising administering a compound of the formula (I):

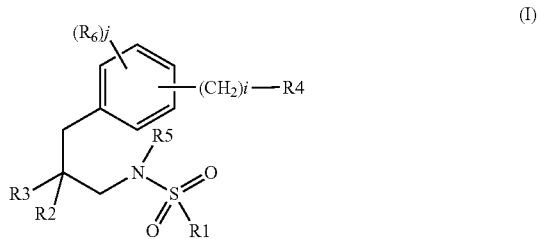

in which formula (I):
R1 represents a group of the formula: —X—(Y)$_m$, in which:
—X— represents an aryl, cycloalkyl, heteroaryl, alkyl or heterocyclyl group;
Each of the groups Y, which may be identical or different, independently represents a halogen atom or an -alkyl, —O-alkyl, —CO-alkyl, —NO$_2$, —O-perhaloalkyl, —S(O)$_q$-alkyl or -perhaloalkyl group, or two groups Y together form an aryl or heteroaryl group fused to the phenyl nucleus to which they are attached;
m represents an integer chosen from 0, 1, 2, 3, 4 and 5;
R2 and R3 together form a cycloalkyl or heterocyclyl group optionally substituted by one or more alkyl groups;
R4 represents a group of the formula -Z-(alkyl)$_n$-T$_p$
in which
-Z- represents —O— or a group —S(O)$_q$— or, if n=p=0, a halogen atom or an —OH group;
T represents a cycloalkyl, heterocyclyl or heteroaryl group;
n represents an integer chosen from 0 and 1;
p represents an integer chosen from 0 and 1;
i represents an integer greater than or equal to 2;
R5 represents a hydrogen atom or an alkyl group, optionally substituted by one or more cycloalkyl groups;
each of the groups R6, which may be identical or different, independently represents a group chosen from alkyl, O-alkyl, a halogen atom and a —CN, —NO$_2$, —CO-alkyl, —CO$_2$R, —NRR', —O-perhaloalkyl or -perhaloalkyl group;
j represents an integer chosen between 0, 1, 2, 3 and 4;

R and R', which may be identical or different, independently represent a hydrogen atom or an alkyl group; and
q represents an integer chosen from 0, 1 and 2;
or a tautomeric, enantiomeric, diastereoisomeric or epimeric form thereof, or a pharmaceutically acceptable salt thereof; with the exception of the compounds for which R4 represents an —OH group or an —O-tetrahydropyran group.

2. A method according to claim 1, in which R1 represents a phenyl group optionally substituted by one or more groups, which may be identical or different, chosen from a halogen atom and an -alkyl, —O-alkyl, —CO-alkyl, —NO$_2$, —O-perhaloalkyl, —S(O)$_q$-alkyl or -perhaloalkyl group, or two substituents together form a phenyl or pyridyl group fused to the phenyl nucleus to which they are attached; or R1 represents a cycloalkyl, heteroaryl or alkyl group.

3. A method according to claim 1, in which R1 represents a phenyl group substituted by at least one halogen atom.

4. A method according to claim 1, in which R2 and R3 together form a cycloalkyl group, optionally substituted by one or more alkyl groups; or R2 and R3 together form a heterocyclyl group.

5. A method according to claim 1, in which R4 represents a group of the formula -Z-(alkyl)$_n$-T$_p$ in which
Z represents —O— or a group —S(O)$_q$— or, if n=p=0, a halogen atom or an —OH group;
i represents 2;
n represents an integer chosen from 0 and 1;
p represents an integer chosen from 0 and 1; and
T represents a cycloalkyl, heterocyclyl or heteroaryl group.

6. A method according to claim 1, in which Z represents a group —S(O)$_q$— in which q=0 or 2.

7. A method according to claim 1, in which R5 represents a hydrogen atom or an alkyl group, optionally substituted by one or more cycloalkyl groups.

8. A method according to claim 1, in which R and R', which may be identical or different, independently represent a hydrogen atom or an alkyl group.

9. A method according to claim 1, in which i=2.

10. A method according to claim 1, in which j=0.

11. A method according to claim 1, in which the group —(CH$_2$)$_i$R4 is in the para position.

12. A method according to claim 1, in which the compounds are chosen from:
2,4-dichloro-N-[(1-{4-[2-(cyclopropylmethoxy)ethyl]benzyl}cyclobutyl)methyl]benzenesulfonamide;
4-chloro-N-[(1-{4-[2-(cyclopropylmethoxy)ethyl]benzyl}cyclobutyl)methyl]benzenesulfonamide;
N-[(1-{4-[2-(cyclopropylmethoxy)ethyl]benzyl}cyclobutyl)methyl]-4-methylbenzenesulfonamide;
N-[(1-{4-[2-(cyclopropylmethoxy)ethyl]benzyl}cyclobutyl)methyl]naphthalene-1-sulfonamide;
N-[(1-{4-[2-(cyclopropylmethoxy)ethyl]benzyl}cyclobutyl)methyl]-4-methoxybenzenesulfonamide;
4-chloro-N-[(1-{4-[2-(cyclopentyloxy)ethyl]benzyl}cyclobutyl)methyl]benzenesulfonamide;
2,4-dichloro-N-[(1-{4-[2-(cyclopentyloxy)ethyl]benzyl}cyclobutyl)methyl]benzenesulfonamide;
N-[(1-{4-[2-(cyclopentyloxy)ethyl]benzyl}cyclobutyl)methyl]-4-methylbenzenesulfonamide;
N-[(1-{4-[2-(cyclopentyloxy)ethyl]benzyl}cyclobutyl)methyl]-4-methoxybenzenesulfonamide;
N-[(1-{4-[2-(cyclopentyloxy)ethyl]benzyl}cyclobutyl)methyl]naphthalene-1-sulfonamide;
4-chloro-N-[(1-{4-[2-(cyclopentylthio)ethyl]benzyl}cyclobutyl)methyl]benzenesulfonamide;
2,4-dichloro-N-[(1-{4-[2-(cyclopentylthio)ethyl]benzyl}cyclobutyl)methyl]benzenesulfonamide;
N-[(1-{4-[2-(cyclopentylthio)ethyl]benzyl}cyclobutyl)methyl]-4-methylbenzenesulfonamide;
N-[(1-{4-[2-(cyclopentylthio)ethyl]benzyl}cyclobutyl)methyl]-4-methoxybenzenesulfonamide;
N-[(1-{4-[2-(cyclopentylthio)ethyl]benzyl}cyclobutyl)methyl]naphthalene-1-sulfonamide;
4-chloro-N-[(1-{4-[2-(methylthio)ethyl]benzyl}cyclobutyl)methyl]benzenesulfonamide;
2,4-dichloro-N-[(1-{4-[2-(methylthio)ethyl]benzyl}cyclobutyl)methyl]benzenesulfonamide;
4-methyl-N-[(1-{4-[2-(methylthio)ethyl]benzyl}cyclobutyl)methyl]benzenesulfonamide;
4-methoxy-N-[(1-{4-[2-(methylthio)ethyl]benzyl}cyclobutyl)methyl]benzenesulfonamide;
N-[(1-{4-[2-(methylthio)ethyl]benzyl}cyclobutyl)methyl]naphthalene-1-sulfonamide;
4-chloro-N-[(1-{4-[2-(cyclopentylsulfonyl)ethyl]benzyl}cyclobutyl)methyl]benzenesulfonamide;
2,4-dichloro-N-[(1-{4-[2-(cyclopentylsulfonyl)ethyl]benzyl}cyclobutyl)methyl]benzenesulfonamide;
N-[(1-{4-[2-(cyclopentylsulfonyl)ethyl]benzyl}cyclobutyl)methyl]-4-methylbenzenesulfonamide;
N-[(1-{4-[2-(cyclopentylsulfonyl)ethyl]benzyl}cyclobutyl)methyl]-4-methoxybenzenesulfonamide;
N-[(1-{4-[2-(cyclopentylsulfonyl)ethyl]benzyl}cyclobutyl)methyl]naphthalene-1-sulfonamide;
4-chloro-N-[(1-{4-[2-(methylsulfonyl)ethyl]benzyl}cyclobutyl)methyl]benzenesulfonamide;
2,4-dichloro-N-[(1-{4-[2-(methylsulfonyl)ethyl]benzyl}cyclobutyl)methyl]benzenesulfonamide;
4-methyl-N-[(1-{4-[2-(methylsulfonyl)ethyl]benzyl}cyclobutyl)methyl]benzenesulfonamide;
4-methoxy-N-[(1-{4-[2-(methylsulfonyl)ethyl]benzyl}cyclobutyl)methyl]benzenesulfonamide;
N-[(1-{4-[2-(methylsulfonyl)ethyl]benzyl}cyclobutyl)methyl]naphthalene-1-sulfonamide;
N-({1-[4-(2-tert-butoxyethyl)benzyl]cyclopentyl}methyl)-4-methylbenzenesulfonamide;
4-chloro-N-[(1-{4-[2-(pyrid-2-yloxy)ethyl]benzyl}cyclopentyl)methyl]benzenesulfonamide; and
N-({1-[4-(2-chloroethyl)benzyl]cyclobutyl}methyl)-2,3,4,5,6-pentafluorobenzenesulfonamide.

13. A method according to claim 1, wherein the compound retinopathy and which comprises specifically inhibiting caspase-10 in the patient.

14. Compound of the formula (I)

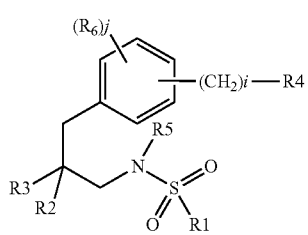

in which:
R1 represents a group of the formula: —X—(Y)$_m$, in which:
—X— represents an aryl, cycloalkyl, heteroaryl, alkyl or heterocyclyl group;
each of the groups Y, which may be identical or different, independently represents a halogen atom or an -alkyl, —O-alkyl, —CO-alkyl, —NO$_2$, —S(O)$_q$-alkyl, —O-perhaloalkyl or -perhaloalkyl group, or two groups Y together form an aryl or heteroaryl group fused to the phenyl nucleus to which they are attached;

m represents an integer chosen from 0, 1, 2, 3, 4 and 5;

R2 and R3 together form a cycloalkyl or heterocyclyl group optionally substituted by one or more alkyl groups;

R4 represents a group of the formula -Z-(alkyl)$_n$-T$_p$ in which

Z represents —O— or a group —S(O)$_q$— or, if n=p=0, a halogen atom;

n represents an integer chosen from 0 and 1;

p represents an integer chosen from 0 and 1;

T represents a cycloalkyl, heterocyclyl or heteroaryl group;

i represents an integer greater than or equal to 2;

R5 represents a hydrogen atom or an alkyl group, optionally substituted by one or more cycloalkyl groups;

each of the groups R6, which may be identical or different, independently represents a group chosen from alkyl, O-alkyl and a halogen atom, or a —CN, —NO$_2$, —CO-alkyl, —CO$_2$R, —NRR', —O-perhaloalkyl or -perhaloalkyl group;

j represents an integer chosen between 0, 1, 2, 3 and 4;

R and R', which may be identical or different, independently represent a hydrogen atom or an alkyl group; and q represents an integer chosen from 0, 1 and 2;

or a tautomeric, enantiomeric, diastereoisomeric or epimeric form thereof, or a pharmaceutically acceptable salt thereof, with the exception of the compounds for which R4 represents an —OH group or an —O-tetrahydropyran group.

15. Compound of the formula (I) according to claim 14, for which R1 represents a phenyl group optionally substituted by one or more groups, which may be identical or different, chosen from a halogen atom and an -alkyl, —O-alkyl, —CO-alkyl, —NO$_2$, —S(O)$_2$-alkyl, —O-perhaloalkyl or -perhaloalkyl group, or two substituents together form a phenyl or pyridyl group fused to the phenyl nucleus to which they are attached; or R1 represents a cycloalkyl, heteroaryl or alkyl group.

16. Compound according to claim 14, for which R2 and R3 together form a cycloalkyl group, optionally substituted by one or more alkyl groups; or R2 and R3 together form a heterocyclyl group.

17. Compound according claim 14, for which R4 represents a group of the formula -Z-(alkyl)$_n$-T$_p$ in which Z represents —O— or a group —S(O)$_q$— or, if n=p=0, a halogen atom;

n represents an integer chosen from 0 and 1;

p represents an integer chosen from 0 and 1;

T represents a cycloalkyl, heterocyclyl or heteroaryl group.

18. Compound according to claim 14, for which i=2.

19. Compound according to claim 14, for which R5 represents a hydrogen atom or an alkyl group, optionally substituted by one or more cycloalkyl groups.

20. Compound according to claim 14, for which j=0.

21. Compound according to claim 14, for which R and R', which may be identical or different, independently represent a hydrogen atom or an alkyl group.

22. Compound according to claim 14, for which q represents an integer chosen from 0, 1 and 2.

23. Compound according to claim 14, chosen from:

2,4-dichloro-N-[(1-{4-[2-(cyclopropylmethoxy)ethyl]benzyl}cyclobutyl)-methyl]benzenesulfonamide;

4-chloro-N-[(1-{4-[2-cyclopropylmethoxy)ethyl]benzyl}cyclobutyl)methyl]-benzenesulfonamide;

N-[(1-{4-[2-(cyclopropylmethoxy)ethyl]benzyl}cyclobutyl)methyl]-4-methyl-benzenesulfonamide;

N-[(1-{4-[2-(cyclopropylmethoxy)ethyl]benzyl}cyclobutyl)methyl]naphthalene-1-sulfonamide;

N-[(1-{4-[2-(cyclopropylmethoxy)ethyl]benzyl}cyclobutyl)methyl]-4-methoxybenzenesulfonamide;

4-chloro-N-[(1-{4-[2-(cyclopentyloxy)ethyl]benzyl}cyclobutyl)methyl]benzenesulfonamide;

2,4-dichloro-N-[(1-{4-[2-(cyclopentyloxy)ethyl]benzyl}cyclobutyl)methyl]-benzenesulfonamide;

N-[(1-{4-[2-(cyclopentyloxy)ethyl]benzyl}cyclobutyl)methyl]-4-methylbenzenesulfonamide;

N-[(1-{4-[2-(cyclopentyloxy)ethyl]benzyl}cyclobutyl)methyl]-4-methoxybenzenesulfonamide;

N-[(1-{4-[2-(cyclopentyloxy)ethyl]benzyl}cyclobutyl)methyl]naphthalene-1-sulfonamide;

4-chloro-N-[(1-{4-[2-(cyclopentylthio)ethyl]benzyl}cyclobutyl)methyl]benzenesulfonamide;

2,4-dichloro-N-[(1-{4-[2-(cyclopentyl thiyl]benzyl}cyclobutyl)methyl]benzenesulfonamide;

N-[(1-{4-[2-(cyclopentylthio)ethyl]benzyl}cyclobutyl)methyl]-4-methylbenzenesulfonamide;

N-[(1-{4-[2-(cyclopentylthio)ethyl]benzyl}cyclobutyl)methyl]-4-methoxybenzenesulfonamide;

N-[(1-{4-[2-(cyclopentylthio)ethyl]benzyl}cyclobutyl)methyl]naphthalene-1-sulfonamide;

4-chloro-N-[(1-{4-[2-(methylthio)ethyl]benzyl}cyclobutyl)methyl]benzenesulfonamide;

2,4-dichloro-N-[(1-{4-[2-(methylthio)ethyl]benzyl}cyclobutyl)methyl]benzenesulfonamide;

4-methyl-N-[(1-{4-[2-(methylthio)ethyl]benzyl}cyclobutyl)methyl]benzenesulfonamide;

4-methoxy-N-[(1-{4-[2-(methylthio)ethyl]benzyl}cyclobutyl)methyl]benzenesulfonamide;

N-[(1-{4-[2-(methylthio)ethyl]benzyl}cyclobutyl)methyl]naphthalene-1-sulfonamide;

4-chloro-N-[(1-{4-[2-(cyclopentylsulfonyl)ethyl]benzyl}cyclobutyl)methyl]-benzenesulfonamide;

2,4-dichloro-N-[(1-{4-[2-(cyclopentylsulfonyl)ethyl]benzyl}cyclobutyl)-methyl]benzenesulfonamide;

N-[(1-{4-[2-(cyclopentylsulfonyl)ethyl]benzyl}cyclobutyl)methyl]-4-methyl-benzenesulfonamide;

N-[(1-{4-[2-(cyclopentylsulfonyl)ethyl]benzyl}cyclobutyl)methyl]-4-methoxy-benzenesulfonamide;

N-[(1-{4-[2-(cyclopentylsulfonyl)ethyl]benzyl}cyclobutyl)methyl]naphthalene-1-sulfonamide;

4-chloro-N-[(1-{4-[2-(methylsulfonyl)ethyl]benzyl}cyclobutyl)methyl]benzenesulfonamide;

2,4-dichloro-N-[(1-{4-[2-(methylsulfonyl)ethyl]benzyl}cyclobutyl)methyl]-benzenesulfonamide;

4-methyl-N-[(1-{4-[2-(methylsulfonyl)ethyl]benzyl}cyclobutyl)methyl]benzenesulfonamide;

4-methoxy-N-[(1-{4-[2-(methylsulfonyl)ethyl]benzyl}cyclobutyl)methyl]benzenesulfonamide;

N-[(1-{4-[2-(methylsulfonyl)ethyl]benzyl}cyclobutyl)methyl]naphthalene-1-sulfonamide;

N-({1-[4-(2-tert-butoxyethyl)benzyl]cyclopentyl}methyl)-4-methylbenzenesulfonamide;

4-chloro-N-[(1-{4-[2-(pyrid-2-yloxy)ethyl]benzyl}cyclopentyl)methyl]benzenesulfonamide; and N-({1-[4-(2-chloroethyl)benzyl]cyclobutyl}methyl)-2,3,4,5,6-pentafluorobenzenesulfonamide.

24. Process for the preparation of a compound of the formula (I) of claim 14 with the exception of the compounds for which R4 represents an —OH group or an —O-tetrahydropyran group, comprising the step of preparing a compound of the corresponding formula (I'):

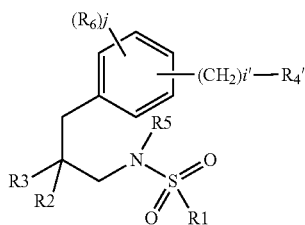
(I')

in which R2, R3, R6 and j are as defined in formula (I) in claim 15, i' represents 0 or i as defined in formula (I) in claim 15 and R4' represents a hydrogen atom, or represents R4 as defined in formula (I) in claim 15 or represents a group -Z-Gp in which Gp represents a leaving group, or alternatively represents a —$CO_2H$ group, starting with a compound of the formula (III):

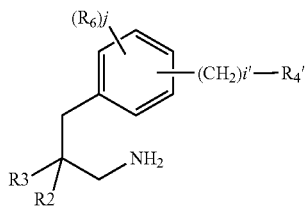
(III)

and reacting with a compound of the formula (IV):

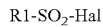
(IV)

$R1-SO_2-Hal$ in which R1 is as defined in formula (I) in claim 15 and Hal represents a halogen atom, optionally followed, if R5 is other than H in formula (I'), by alkylation of the nitrogen atom.

25. Process according to claim 24, in which the compound of the formula (III) is obtained from the compound of the corresponding formula (V)

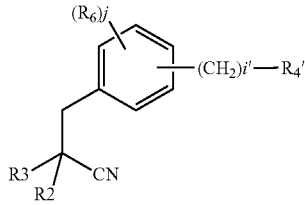
(V)

in which,
R2 and R3 together form a cycloalkyl or heterocyclyl group optionally substituted by one or more alkyl groups;
each of the groups R6, which may be identical or different, independently represents a group chosen from alkyl, O-alkyl and a halogen atom, or a —CN, —$NO_2$, —CO-alkyl, —$CO_2R$, —NRR', —O-perhaloalkyl or -perhaloalkyl group;
j represents an integer chosen between 0, 1, 2, 3 and 4;
R and R', which may be identical or different, independently represent a hydrogen atom or an alkyl group;
and i' and R4' are as defined in formula (I'), via reduction of the nitrile function using any suitable reducing agent.

26. Process according to claim 25, in which the compound of the formula (V) is obtained from the compound of the corresponding formula (VI):

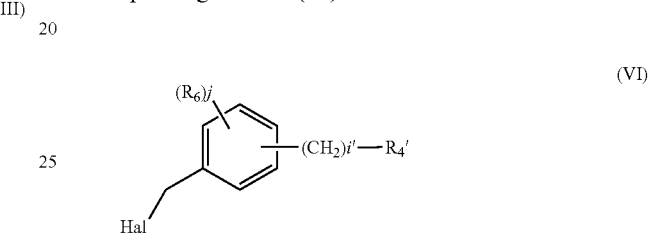
(VI)

in which i' and R4' are as defined in formula (I') and Hal represents a halogen atom, such as chlorine or bromine,
by reacting with a compound of the formula (VII):

(VII)

in which R2 and R3 are as defined in formula (I').

27. Pharmaceutical composition comprising a compound of the general formula (I) as defined in claim 14 and a pharmaceutically acceptable excipient.

28. A compound according to claim 14, wherein Z represents —O— or a group —$S(O)_q$—.

* * * * *

UNITED STATES PATENT AND TRADEMARK OFFICE
CERTIFICATE OF CORRECTION

PATENT NO.        : 8,357,721 B2
APPLICATION NO.   : 11/912461
DATED             : January 22, 2013
INVENTOR(S)       : Claude Lardy et al.

Page 1 of 1

It is certified that error appears in the above-identified patent and that said Letters Patent is hereby corrected as shown below:

In the Claims

Column 48, (Claim 13) line 43 – line 45 reads: "13. A method according to claim 1, wherein the compound retinopathy and which comprises specifically inhibiting caspase-10 in the patient."

Should read: --13. A method according to claim 1, wherein the compound is administered to a newly diagnosed diabetic patient and/or a patient suffering from early retinopathy and which comprises specifically inhibiting caspase-10 in the patient.--.

Column 51, (Claim 24) line 12 reads: "15, i′ represents 0 or i as defined in formula (I) in claim 15 and"

Should read: --14, i′ represents 0 or i as defined in formula (I) in claim 14 and--.

Column 51, (Claim 24) line 14 reads: "formula (I) in claim 15 or represents a group Z-Gp in which"

Should read: --formula (I) in claim 14 or represents a group –Z-Gp in which--.

Column 51, (Claim 24) line 31 reads: "in which R1 is as defined in formula (I) in claim 15 and Hal"

Should read: --in which R1 is as defined in formula (I) in claim 14 and Hal--.

Signed and Sealed this
Twenty-first Day of May, 2013

Teresa Stanek Rea
*Acting Director of the United States Patent and Trademark Office*